United States Patent
Nakayama

(10) Patent No.: US 7,491,492 B2
(45) Date of Patent: Feb. 17, 2009

(54) METHOD OF DETECTING NUCLEOTIDE MUTATIONS

(75) Inventor: Masato Nakayama, Kisarazu (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 10/488,312

(22) PCT Filed: Jul. 30, 2003

(86) PCT No.: PCT/JP03/09692

§ 371 (c)(1),
(2), (4) Date: Sep. 28, 2004

(87) PCT Pub. No.: WO2004/011646

PCT Pub. Date: Feb. 5, 2004

(65) Prior Publication Data

US 2006/0003325 A1 Jan. 5, 2006

(30) Foreign Application Priority Data

Jul. 30, 2002 (JP) ............................. 2002-222133

(51) Int. Cl.
*C12Q 1/68* (2006.01)
*G01N 33/566* (2006.01)
*C07H 21/02* (2006.01)
(52) U.S. Cl. ........................... 435/6; 436/501; 536/23.1
(58) Field of Classification Search .................. None
See application file for complete search history.

(56) References Cited

U.S. PATENT DOCUMENTS 4,343,684 A 8/1982 Lechtzen (Continued)

FOREIGN PATENT DOCUMENTS

JP 56-152958 A 11/1981

(Continued)

OTHER PUBLICATIONS

1998/1999 New England Biolabs Catalog, cover and pp. 79, 90-92, 116-121.*

(Continued)

*Primary Examiner*—Young J Kim
*Assistant Examiner*—Samuel Woolwine

(57) ABSTRACT

The present invention provides a nucleotide mutation detection method wherein primers having a nucleotide sequence complementary to part of the nucleic acids to be detected and also having a nucleotide sequence, which is complementary to the nucleotide sequence just upstream from a nucleotide site corresponding to the mutation site of the nucleotide sequence formed at the 3' end, added to the 5' end, are produced so that so that the nucleotide site corresponding to the mutation site of the nucleic acids to be detected including the nucleotide mutation is located within the nucleotide sequence formed at the 3' end after elongation; a target is produced by subjecting the primers to an elongation reaction using polymerase or Klenow enzyme; the target is then denatured to a single strand, and is subjected to a hybridization reaction with a probe that has the nucleotide complementary to the mutation site of the nucleic acids present in the 3' end region and then to a ligation reaction, whereby it is enable to determine and assay a nucleotide located at a specific position in a nucleotide sequence of DNA or RNA and to analyze rapidly a variety of mutations including single nucleotide mutations, short nucleotide tandem repeat mutations, nucleotide deletion mutations, nucleotide insertion mutations, translocation mutations and so on.

12 Claims, 16 Drawing Sheets

U.S. PATENT DOCUMENTS

| | | | |
|---|---|---|---|
| 4,840,893 A | | 6/1989 | Hill et al. |
| 4,857,831 A | | 8/1989 | Davies et al. |
| 5,108,576 A | | 4/1992 | Malmros et al. |
| 5,614,004 A | | 3/1997 | Wachi |
| 5,627,054 A | * | 5/1997 | Gillespie ................... 435/91.2 |
| 5,866,321 A | | 2/1999 | Matsue et al. |
| 5,873,992 A | | 2/1999 | Glezen |
| 6,063,573 A | * | 5/2000 | Kayyem ........................ 435/6 |
| 6,093,370 A | | 7/2000 | Yasuda et al. |
| 6,114,121 A | | 9/2000 | Fujiwara et al. |
| 6,126,800 A | | 10/2000 | Caillat et al. |
| 6,150,095 A | | 11/2000 | Southern et al. |
| 6,312,892 B1 | * | 11/2001 | Barany et al. .................. 435/6 |
| 6,340,568 B2 | | 1/2002 | Hefti |
| 6,342,359 B1 | | 1/2002 | Lee et al. |
| 6,368,851 B1 | | 4/2002 | Baumann et al. |
| 6,403,319 B1 | | 6/2002 | Lizardi et al. |
| 6,749,731 B2 | | 6/2004 | Kobori et al. |
| 6,821,406 B2 | | 11/2004 | Kobori et al. |
| 6,893,824 B2 | | 5/2005 | Ito |
| 6,916,614 B1 | | 7/2005 | Takenaka et al. |
| 2002/0090649 A1 | * | 7/2002 | Chan et al. .................... 435/7.1 |
| 2003/0119004 A1 | * | 6/2003 | Wenz et al. ..................... 435/6 |
| 2004/0152097 A1 | | 8/2004 | Takenaka |
| 2004/0185462 A1 | | 9/2004 | Miyahara et al. |
| 2005/0028906 A1 | | 2/2005 | Kobori et al. |

FOREIGN PATENT DOCUMENTS

| | | |
|---|---|---|
| JP | 9288080 | 11/1997 |
| JP | 11-503019 | 11/1999 |
| WO | WO 96/31622 A1 | 10/1996 |
| WO | WO 98/03673 A1 | 1/1998 |
| WO | WO 01/12856 A2 | 2/2001 |
| WO | WO 2004/011646 A1 | 2/2004 |

OTHER PUBLICATIONS

Freeman. B.D. et al., Template-Directed Dye-Terminator Incorporation with Fluorescence Polarization Detection for Analysis of Single Nucleotide Polymorphisms Implicated in Sepsis, Journal of Molecular Diagnostics, 4(4): 209-215 (Nov. 2002).

Variom Biotechnology AG, Genespector rapid genotyping kits.

Bain, C. D. et al., Formation of Monolayer Films by the Spontaneous Assembly of Organic Thiols from Solution onto Gold, J. Am. Chem. Soc., 111: 321-335 (1989).

Gooding, J. J. et al., Platinum-Catalyzed Enzyme Electrodes Immobilized on Gold Using Self-Assembled Layers, Anal. Chem, 70: 2396-2402 (1998).

Takanaga, Shigeori et al., "Synthesizing the Electrochemical Threading Type Intercalator and Applying the Electrochemical Threading Type Intercalator to a DNA Sensor," Proceedings of the Japan Society for Analytical Chemistry, pp. 137-138 (1996).

European Office Action for corresponding European Patent Application No. 03771437.5 dated Apr. 10, 2007 (in English).

* cited by examiner

SINGLE BASE MUTATION:

REPEATED BASE SEQUENCE MUTATION :

BASE DELETION MUTATION:

TRANSLOCATION MUTATION DETECTION :

METHOD OF DETECTING NUCLEOTIDE MUTATIONS

TECHNICAL FIELD

The present invention relates to a technique of rapidly analyzing a variety of mutations including single nucleotide polymorphism, short nucleotide tandem repeat mutations, nucleotide deletion mutations, nucleotide insertion mutations and translocation mutations by determining and quantitating a nucleotide type at a specific location in the nucleotide sequence of DNA, RNA or the like.

BACKGROUND ART

Currently, typical methods of assaying mutations in the nucleotide sequence of DNA include Single-strand conformation polymorphism (SSCP) and DNA sequencing.

The SSCP method, developed by M. Orita et al in 1989, is a method to analyze polymorphisms by utilizaing the fact that single-strand DNA adopts a higher-order structure dependent on the nucleotide sequence, and the structure are detected as differences in mobility by polyacrylamide gel electrophoresis. It is also called PCR-SSCP since DNA fragments amplified by PCR are often employed.

Because this method uses electrophoresis, however, it cannot identify the location and the type of nucleotide of the mutation. In addition, SSCP is non-qunatitative analysis and difficult to rapidly analyze many samples at the same time.

There are several different kinds of DNA sequencing methods, but the fundamental one is Sanger's method, developed in 1975. In this method, DNA fragment of interest is converted to a single strand, and the complementary strand against to a fluorescent labeled primer is elongated by DNA polymerase in the presence of following reagents; fluorescent labeled primers that recognizes the 5' upstream sequence from the site of interest, four types of deoxynucleotide (dNTP) including adenine (dATP), thymine (dTTP), guanine (dGTP) and cytosine (dCTP), and one type of dideoxynucleotide. DNA elongation will progress when dNTP (a constituent of DNA) is incorporated until a ddNTP is incorporated. Because of a hydroxyl group added at the binding site of the next nucleotide, the polymerization reaction is blocked, and the DNA can no longer be elongated. As a result, multiple DNA fragments are produced with specific bases at their ends. In this method, four different samples are produced using four types of ddNTP, and the nucleotide sequence can be analyzed by performing electrophoresis and reading the resulting DNA bands in sequence.

However, although this method is suited to analyzing a broad range of nucleotide sequences from DNA fragments, it is not convenient enough when the object of study is a mutation at a specific site.

Dye-labeled oligonucleotide ligation (DOL) is another method of detecting nucleotide mutations. DOL utilizes the binding of two oligonucletides with DNA ligase. Following two types of oligonucleotides are prepared; an oligo probe complementary to a sequence labeled with fluorescein at the 5' end and ending one nucleotide upstream from the SNP site, and an oligo probe fluorescently labeled at the 3' end which includes the SNP region and is complementary to the sequence downstream therefrom. According to the differences in the complementary nucleotide of the SNP region, the second probe is labeled with different fluorescent dye such as ROX or TAMRA. When these probes and DNA ligase are added in PCR reaction mixture, the number of probes joined by ligase is increased as the PCR reaction progress. Since the only joined probes are those which are complementary to the SNP region, excitation of fluorescein allows the SNP to be determined based on what fluorescent wavelength emitted as a result of fluorescence resonance energy transfer (FRET). DOL assay is extremely simple because all reactions are performed simultaneously in one tube, but unfortunately it is not suitable for multiple specimens processing.

Another ligation method which has been developed for detecting nucleotide mutations is Genespector (trade name; Variom Biotechnology AG analysis kit). In this method, probes are fixed on a solid surface and the detection is achieved by a ligation reaction following a hybridization reaction using the DNA PCR product, a signal probe and an allele-specific detection probe.

However, this method has problems of detection sensitivity of the nucleotide mutation and speed of the mutation analysis.

Hereinafter, an invention to determine and assay a nucleotide type at a specific location in DNA or RNA, and rapidly analyzes a variety of mutations including single nucleotide polymorphism, repeated nucleotide sequence mutations, nucleotide deletion mutations, nucleotide insertion mutations and translocation mutations is presented.

DISCLOSURE OF THE INVENTION

The present invention resolves the aforementioned issues by providing a method of detecting nucleotide mutations comprising the following steps (A)-(D):

(A) a step of producing primers (elongatable primers) having (1) a nucleotide sequence complementary to part of the nucleic acids to be detected, including the mutation site, and (2) a nucleotide sequence added to the 5' end, which is complementary to the nucleotide sequence formed at the 3' end after elongation where is just upstream of the mutation nucleotide, wherein (3) the primers are produced so that the mutation site will be located in the down stream after the elongation;

(B) a step of producing the target by subjecting the primers to an elongation reaction using polymerase or Klenow enzyme;

(C) a step of then denaturing the target to a single strand, and subjecting this target to a hybridization reaction with a probe that has the complementary sequence which includes the mutation site at the 3' end.

The present invention also provides a detection system for nucleotide mutations, characterized by the use of the aforementioned method.

BEST MODE FOR CARRYING OUT THE INVENTION

[Method of Detecting Nucleotide Mutations]

The method of detecting nucleotide mutations of the present invention is explained in detail below based on preferred embodiments.

Figure 1:
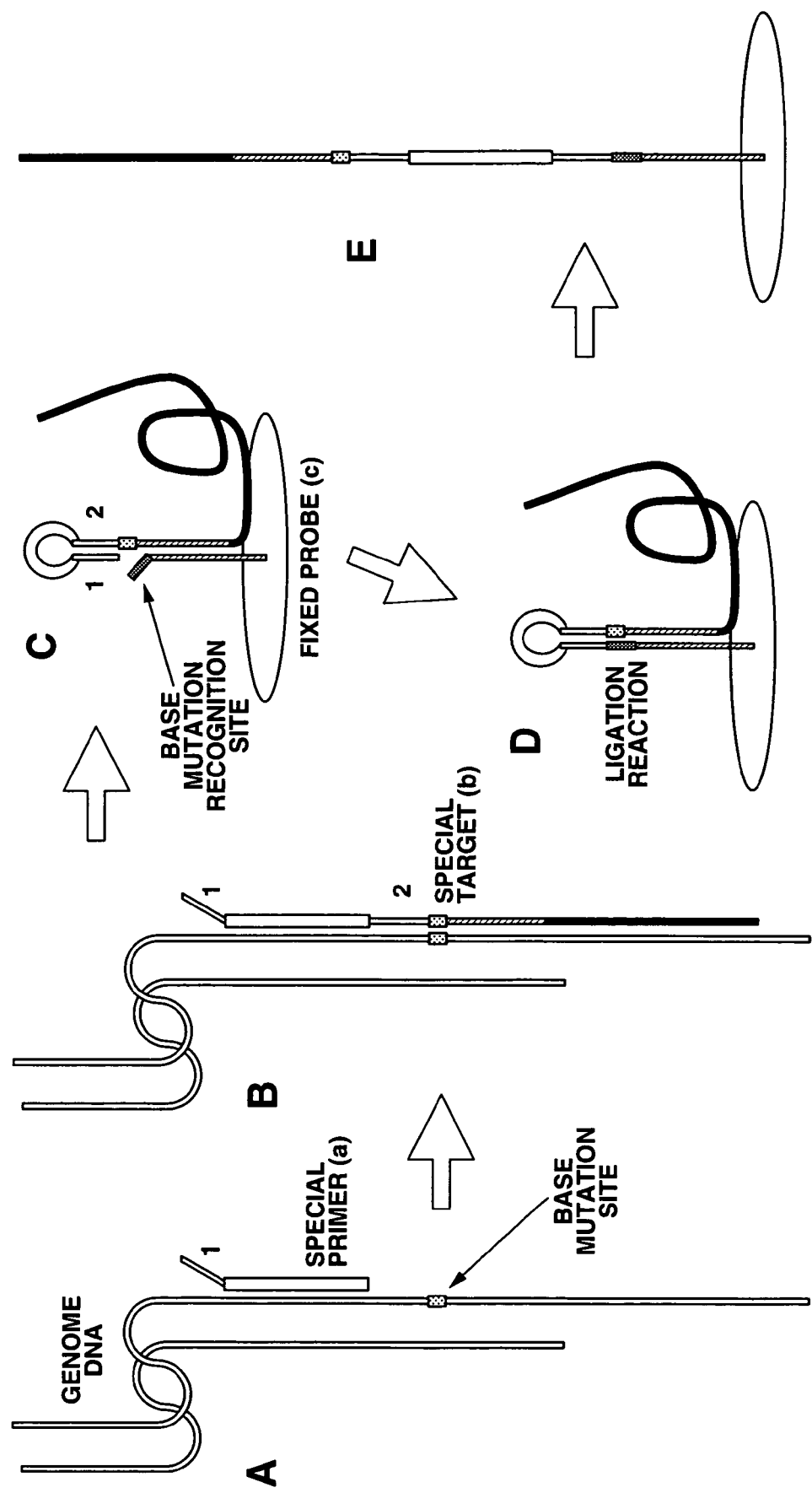
FIG. 1 is a conceptual drawing explaining the basic principles of the detection method of the present invention.

As shown in FIG. 1, the basic principles of the detection method of the present invention comprise (A) the preparation of a special primer, (B) an elongation reaction of the special primer, (C) denaturing and hybridization with a fixed probe, (D) a ligation reaction, and (E) washing and detection to detect a nucleotide mutation in genome DNA or other nucleic acids. These steps are described in more detail below.

[A] Preparation of Special Primer

Primer (hereafter called "special primer (a)") complementary to the genome which is the object of detection is synthesized. In addition to the complementary sequence for binding to the genome, a sequence 1 which is complementary to sequence 2 formed after elongation is added to the 5' end of this special primer (a).

Special primer (a) is designed so that the mutation site will be located in down stream after elongation reaction described below. The resulting special primer (a) has a complementary sequence to the part of the target genome, as well as a nucleotide sequence added to the 5' end which is complementary to the elongated sequence starting just down stream of this primer to the one nucleotide before the mutation site.

One special primer (a) is formed for each nucleotide mutation to be detected, and a target (and multiple replications of the same target by repeated elongations, hereunder sometimes called "special target (b)") is prepared using special primer (a) by the elongation reaction described below. This special target includes mutation site and self complementary region, and it can be provided for both hybridization and ligation reaction with a probe.

[B] Special Primer Elongation Reaction

Using the aforementioned special primer (a), an elongation reaction is performed with enzymes (polymerase—either DNA polymerase or RNA-dependent DNA polymerase—or Klenow enzyme). Special target (b) is prepared in this way. Special target (b) can be prepared by any method desired, such as methods 1)-3) below.

1) Fix the temperature and prepare the target in a single elongation reaction.

Figure 2:
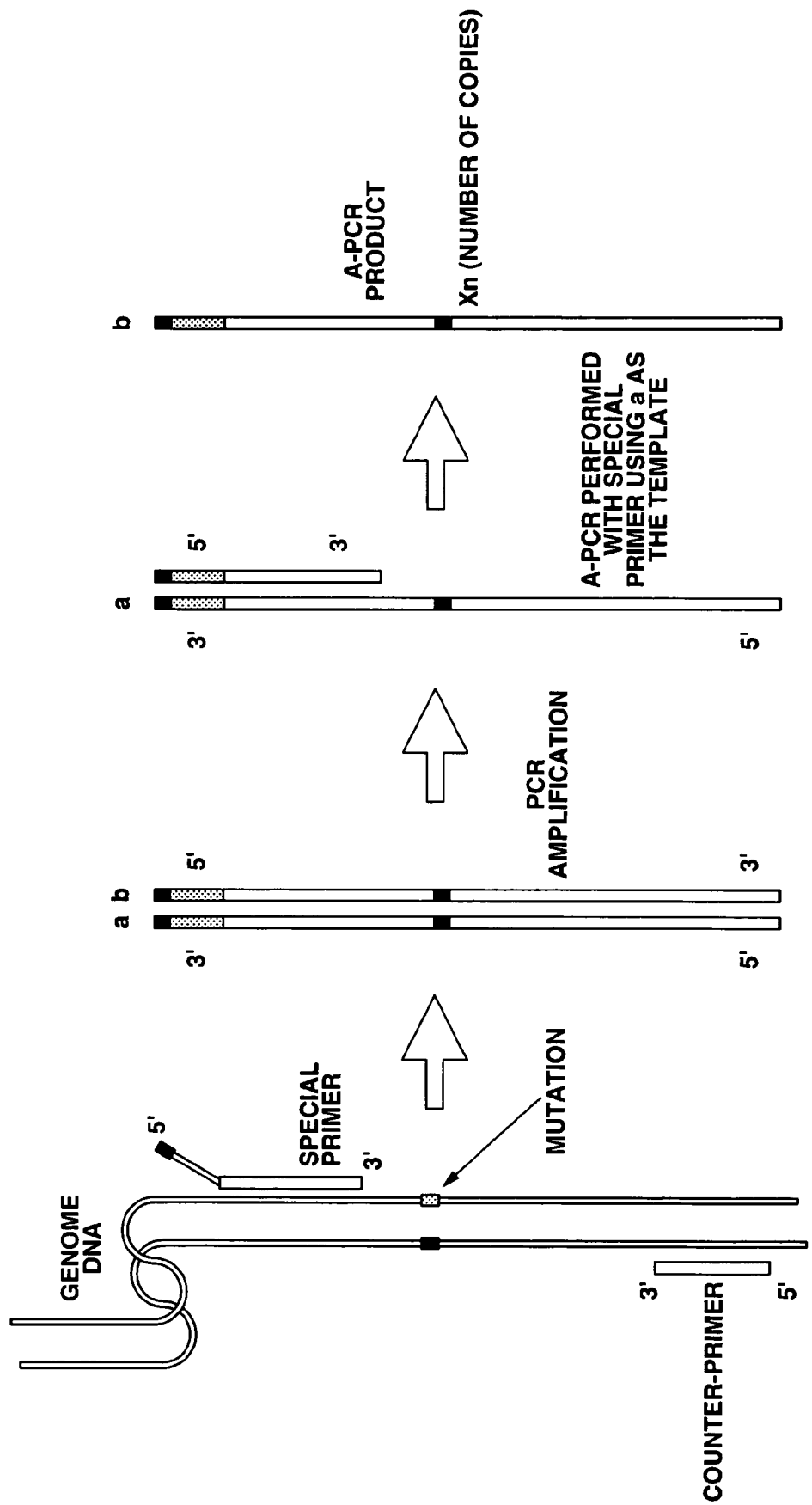
FIG. 2 shows an example of the method of producing a special target according to the detection method of the present invention.

2) Amplify the target by PCR using a counter-primer (see FIG. 2).

3) Prepare the desired target by Asymmetrical-PCR (called A-PCR below) (see FIG. 2).

Particularly when PCR and A-PCR are used, the molecular number and nucleotide strand length of the special target can be controlled at will, allowing for greater detection sensitivity and less effect from non-specific binding, thus resulting in greater detection efficiency. Appropriate design of the counter-primer makes it possible to control the length of the special target, improve hybridization efficiency, suppress non-specific binding and the like.

The special target can be designed so that it forms a loop by self-complementary binding, enabling non-specific binding to be controlled even in the case of long nucleotide chains, and enhancing the specificity of the hybridization reaction. Specifically, great sensitivity can be achieved by increasing the length of the special target. Recognition sensitivity can also be enhanced by adding a new reaction step in which a second target (enhancer target) is applied (enhancing hybridization) to the loop region formed by self-complementary binding on the special target.

(Design of the Special Primer)

Figure 7:
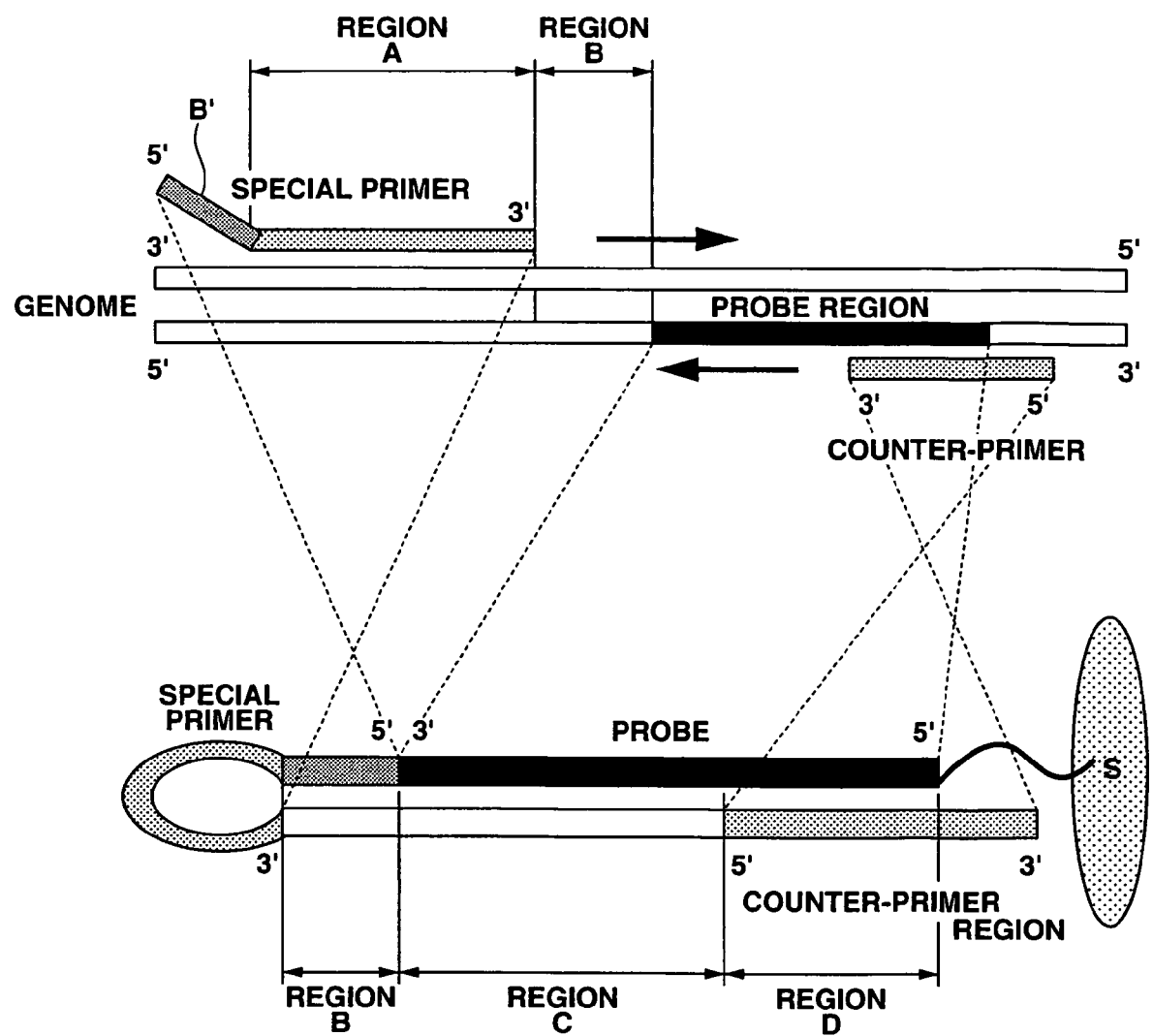
FIG. 7 is a conceptual drawing explaining the designs of the special primers, counter-primers and probes of the detection method of the present invention.

In the present invention, the special primer should be designed as follows (see FIG. 7).

i) Oligonucleotide: total sequence length 33 nucleotides or more ii) 5' end nucleotide: phosphoric acid group added iii) Structure: the special primer is made up of two types of structural regions. it comprises sites of region A, which hybridizes preferentially with genome DNA, and sites of region B', which has a sequence complementary to region B immediately downstream from 3' end. This region B is obtained by the elongation reaction of the special primer.

iv) The sequence length of region B' should be at least 13 nucleotides, and the Tm setting should be about 50° C. (±10° C.).

v) The sequence length of region A should be at least 20 nucleotides, and the Tm setting should be at least 60° C.

vi) The Tm of the site of region B' should always be more than 5° C. lower than that of Region A (this temperature difference allows the sites of region A to be hybridized preferentially over the sites of region B' in the elongation reaction from genome DNA).

vii) When region B, just downstream of the special primer which is produced after the elongation reaction, is hybridized with the region B', the region A forms a loop (if the sites of region B' and region B are well hybridized, complementary binding within the fold does not affect the formation of the loop). When this loop is formed in the target, commonly observed non-specific binding between probe and DNA target correlated to its nucleotide length is suppressed.

viii) The special primer is designed so that the 5' adjacent nucleotide position in newly formed elongated region from the hybrid region formed in vii) becomes the mutation nucleotide position.

ix) The elongated region (region C) newly formed downstream from the hybrid region formed in vii) above is complementary to the probe, and has at least 20 or more nucleotides.

(Design of the Counter-Primer)

In the present invention, the counter-primer should be designed, and an elongation reaction performed by PCR or A-PCR as follows (see FIG. 7).

i) Oligonucleotide: 20 nucleotides length or more ii) Tm setting should be 60° C. or more iii) The Tm setting of the counter-primer should always be as follows: region A by special primer>counter primer region>region B' by special primer. This Tm difference allows the special primer alone to be preferentially elongated if the temperature is set above the counter-primer Tm when performing A-PCR using PCR product obtained from genome DNA as the template.

iv) The position for the counter-primer hybridization should be set so that the 3' end of the counter primer (the 5' end of the counter primer region) is removed more than 13 nucleotides upstream from the 3' end of the probe. (If counter-primer removal process is omitted in special target production, the special target and the counter-primer might be hybridized, and block the probe and desired special target hybridization process. Therefore, in order to circumvent above possibility, the minimum necessary nucleotides (13 nucleotides) for hybridization between the special target and probe is maintained. The counter-primer is not necessary to be positioned within the probe region, and may also be positioned up strem of the probe region.

v) The Tm of the region C where the special target and probe is hybridized, should be greater than that of region D where the counter-primer and the special target. (If the counter-primer has a complementary sequence within the special target region, hybridization between the special target and the counter-primer might interfere with the hybridization between the probe and the special target. Therefore it is desirable to set the Tm of the special target against the probe higher than that against counter-primer, so that the special target is more stably hybridized with the probe than the counter-primer.

[C] Denaturing and Hybridization with the Fixed Probe

Reaction mixture containing the special target (b) produced by the elongation reaction is thermally denatured and the special target (b) becomes single strand. Next, special target (b) is hybridized with fixed probe (c) (having a complementary sequence and the mutation site at the 3' end). At the same time, the 5' end strand (sequence 1) and the strand (sequence 2) formed after the elongation reaction hybridize each other, and the original primer part of special target (b) forms an intermolecular loop. As a result, the nucleotide at the 3' end of the probe and the 5' end of the hybridized special target are now next to each other.

(Design of Probes)

Probes can be obtained by synthesizing oligonucleotides having corresponding nucleotides of individual mutation at its 3' end and complementary sequence to the special target.

The probes should consist of two or more types so that multiple mutations can be determined and quantified simultaneously. By thus synthesizing multiple types of probes, it is possible to simultaneously determine and assay nucleotide mutations (multiple types) at specific sites with multiple genomes, which is the goal of detection.

The oligonucleotide sequence of the probe can be selected at will from within the range of sequence lengths that can specifically identify the intended recognition site.

The probe should also contain electrode fixing element so that it can be easily fixed to an electrode. Since this electrode fixing element cannot be located on the side where the ligation reaction will be carried out in the next step, it is formed only to the 5' end of the oligonucleotide.

The electrode fixing element should be capable of binding to the aforementioned electrode by a reaction. Concrete examples of the electrode fixing element include thiol groups, biotin residues, amino groups and groups including any of these, and the element can be selected according to the electrode surface used for fixing the probe.

The probe should also have a linker between the oligonucleotide and the electrode fixing element. Having this linker increases the degree of freedom to the oligonucleotide during hybridization, and enhances hybridization efficiency, allowing for highly precise detection.

A hydrocarbon chain, de-based nucleotide chain or the like is desirable as the linker.

In the present invention, designing the probe in the following way is particularly desirable from the standpoint of good hybridization efficiency of the special target and binding efficiency with the DNA ligase enzyme.

i) Oligonucletide: sequence length 20 nucleotides or more ii) Electrode fixing element: thiol group iii) Linker: alkane of carbon number 6 iv) Site for mutation detection is set at the 3' end

Desirable method of utilizing designed probes as described above is fixing single probe on single electrode so that one type of probe corresponds to one electrode. In particular, if several probes are fixed on corresponding electrode and integrated, it is possible to detect multiple mutations in a sample by single operation.

Desirable electrode for probe fixing is having binding characteristics by reaction with fixing element of probe. Desirable combinations of electrode and electrode binding elements are given as (1)-(3) below.

(1) (Electrode) At least the surface is made of gold (Au)

(Electrode fixing element) Includes a thiol group (—SH)

(2) (Electrode) At least the surface is either avidin or streptavidin (Electrode fixing element) Includes a biotin residue (3) (Electrode) At least the surface has a carboxyl group (—COOH)

(Electrode fixing element) Includes an amino group (—NH$_2$)

Electrodes whose surface, at least, are made of gold include solid gold electrodes and those with gold plated surface over a base made of a material other than gold. Electrodes whose surface, at least, have avidin or streptoavidin. In the case having a carboxyl group, Surface of any desired base is coated by resin having a carboxyl group or the like.

[D] Ligation Reaction

The mutation is recognized in this step. The ligation method uses a linking enzyme solution consisting of a linking enzyme and a buffer.

In the case of a qualification reaction (1-step reaction), those salts required for DNA hybridization, DNA ligase and DNA ligase buffer solution are used as the linking enzyme solution.

In the case of an quantitative reaction (3-step reaction including a washing step), a solution containing those salts required for hybridization is used in the first step (hybridization), while in the third step (ligation), salts which do not allow dissociation (denaturing) of the 2-strand DNA formed by hybridization are included along with DNA ligase and the DNA ligase buffer solution.

The hybridization reaction can also be performed separately from the ligation reaction using a solution containing at least those salts required for hybridization of the nucleic acids. The hybridization reaction can also be carried out simultaneously with the ligation reaction using a synthetic enzyme solution containing at least DNA ligase and a DNA ligase buffer solution.

In this step, the nucleotide (see FIG. 1C) at the nucleotide mutation recognition site will undergo ligation if it is complementary to the nucleotide of the special target which faces it after hybridization, but will not undergo ligation if it is not complementary. The ligation reaction will also not occur if the nucleotide mutation recognition site (3' end of probe) is even one nucleotide short.

[E] Washing and Detection

Following the ligation reaction, washing (denaturing) is performed with a denature reagent to remove special target, genome and the like bound non-specifically to solid-phase surface or fixed DNA.

It is also possible to perform thermal denaturing instead of using a denature reagent.

After the washing process, the amount of DNA remaining on the solid-phase surface is measured. There are no particular limits on the method of measuring the amount of DNA. It can be measured while the DNA is fixed on the solid phase, or by concentration measurement in solution following removal from the solid phase. A method such as applying a reagent which bonds chemically to the DNA can be used for measurement on the solid phase. Alternatively, an electrode can be used as solid phase, and the amount of fixed DNA is measured as the electrical signal by utilizing an electrochemical reagent.

The detection method of the present invention can be used for either quantification or qualification. When the sample DNA contain only one mutation (when the nucleotide mutation sites of all DNA are occupied by the same type of nucleotide), only qualification measurement is required. In this case, steps [C] and [D] above can be combined, and same result as separated steps are obtained.

In the case of quantitative analysis (when genome contains multiple nucleotide types at the mutation site), a washing step is added between aforementioned steps [C] and [D] to remove the unreacted molecules, and the proportions of mutant DNA in the sample can then be measured.

A variety of mutations (single nucleotide polymorphisms, short nucleotide tandem repeat mutations, nucleotide deletion mutations, nucleotide insertion mutations, translocation mutations and the like) can be analyzed in the detection method of the present invention, and these different mutations can be analyzed simultaneously on the same array.

Figure 3:
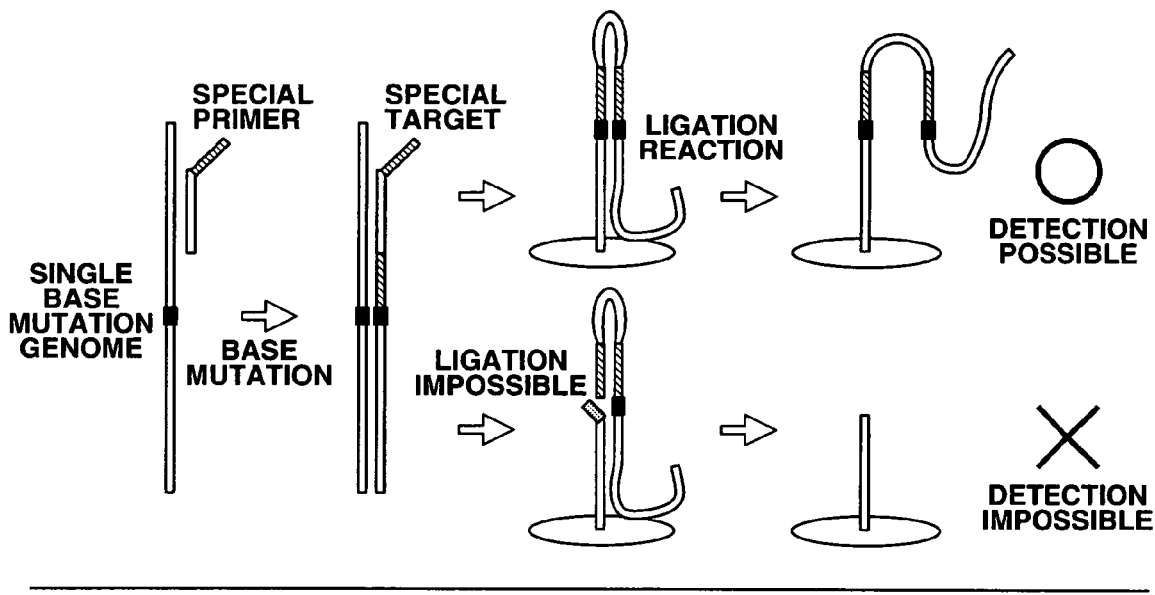
FIG. 3 is an explanatory drawing showing the analysis of single nucleotide polymorphism according to the detection method of the present invention.
Figure 3:
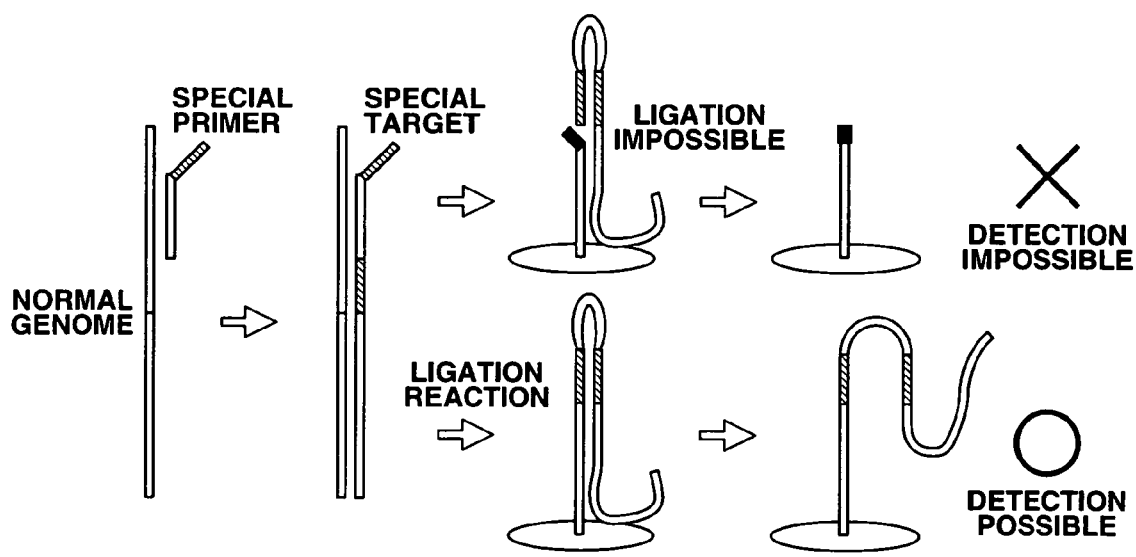

Analysis of a single nucleotide polymorphism according to the detection method of the present invention is explained with reference to FIG. 3.

When the special target has a single nucleotide polymorphism, the ligation reaction occurs only with the mutant probe, resulting in joining of the special target to the probe. As a result, a greater signal is obtained than the signal of the probe before ligation. For the normal probe, no ligation reaction occurs because the ligation site nucleotide is non-complementary, and the signal is the same as for the original probe. The presence or absence of a single nucleotide mutation can be determined based on this difference in signals.

When the special target contains a normal nucleotide at mutation site, the absence of a single nucleotide polymorphism can be determined by the opposite reactions.

Figure 4:
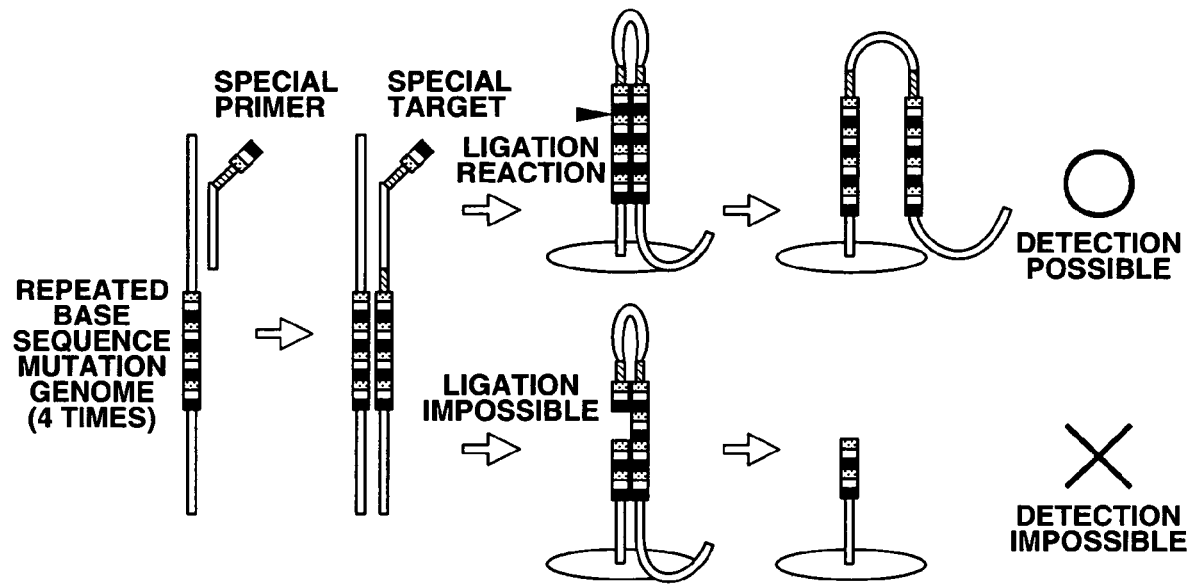
FIG. 4 is an explanatory drawing showing the analysis of repeated nucleotide sequence mutations according to the detection method of the present invention.
Figure 4:
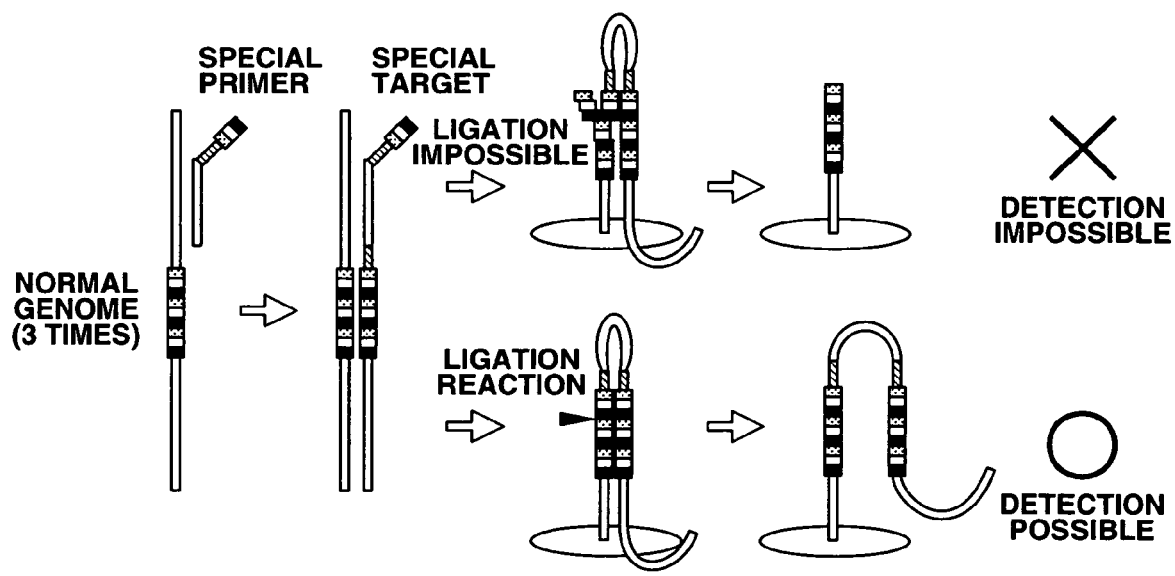

Analysis of a short tandem repeat mutation according to the detection method of the present invention is explained with reference to FIG. 4.

When the special target has a short tandem repeat mutation, the ligation reaction occurs only with the mutant probe, resulting in joining of the special target to the probe. As a result, a greater signal is obtained than the signal of the probe before ligation. For the normal probe, the number of repeated sequence is less than that of the mutant probe, and no ligation reaction occurs because of the missing nucleotides at the ligation site, and the signal after the ligation is the same as before the ligation. The presence or absence of short tandem repeat mutations can be determined based on this difference in signals.

When the special target has normal number of the short tandem repeat, the opposite reactions occur: for the mutant probe, to the extent that the special target has a shorter repeated sequence length, the nucleotides near the 3' end of the mutant probe overlap rather than lining up with the nucleotides near the 5' end of the special target, and no ligation reaction occurs. On the other hand a strong signal is obtained from the resulting ligation between the special target and a normal probe, and mutations can be recognized in this way.

Figure 5:
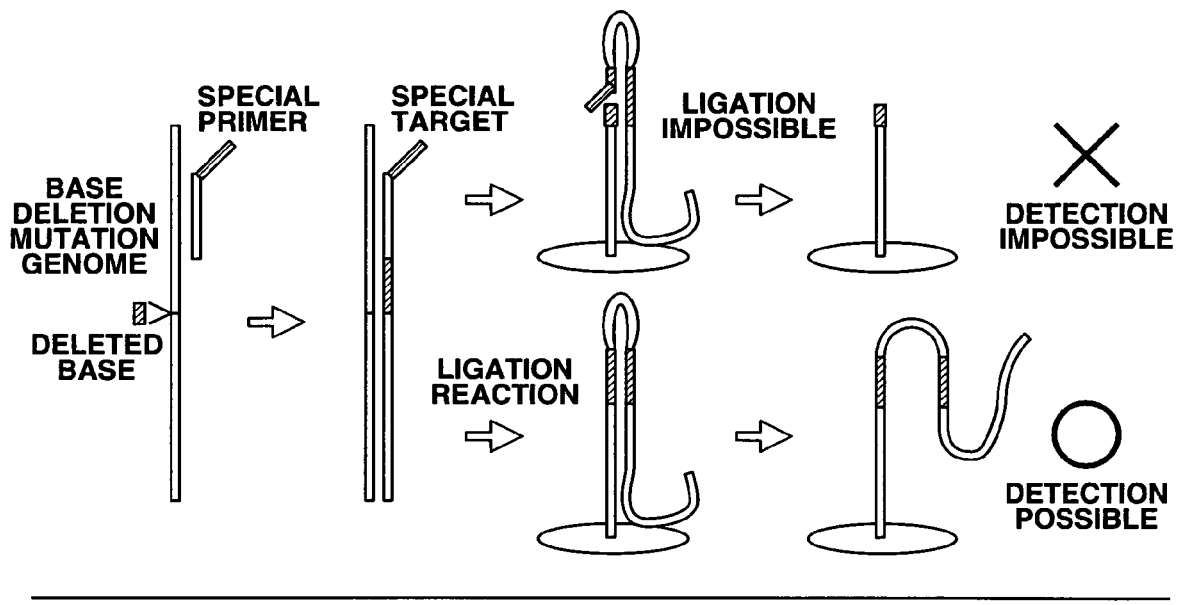
FIG. 5 is an explanatory drawing showing the analysis of nucleotide deletion mutations and insertion mutations according to the detection method of the present invention.
Figure 5:
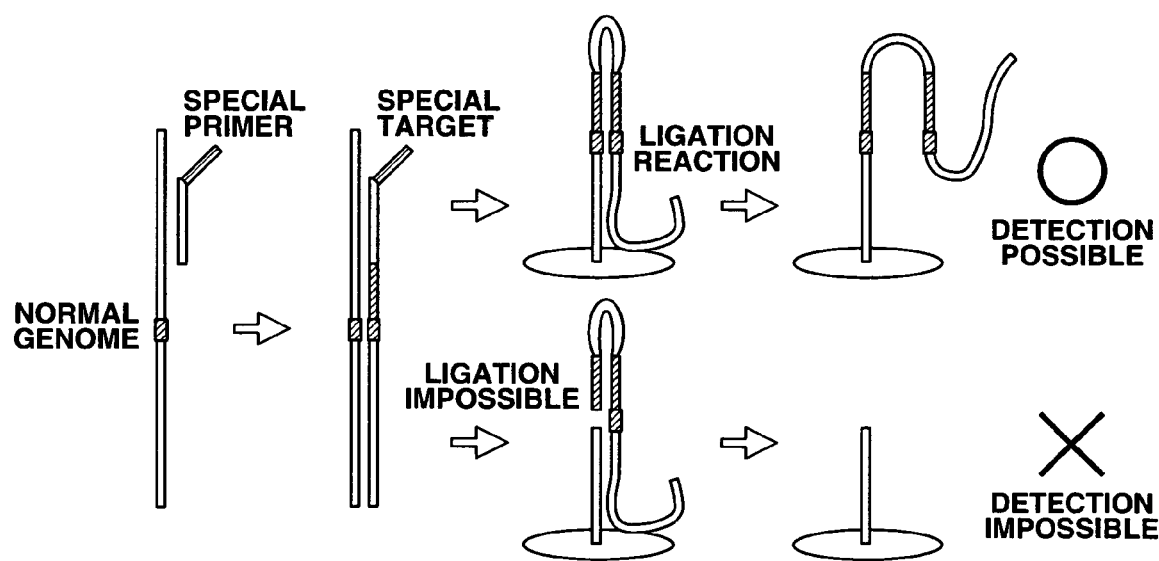

Analysis of nucleotide deletion mutations and nucleotide insertion mutations according to the detection method of the present invention is explained with reference to FIG. 5.

When the special target has a nucleotide deletion mutation, a ligation reaction occurs only with the mutant probe, resulting in joining of the special target to the probe. In this way, a greater signal is obtained than the signal of the probe before ligation. For the normal probe, however, because the probe is longer than the mutant probe by the length of the deleted nucleotide, the nucleotides near the 3' end of the normal probe overlap rather than lining up with the nucleotides near the 5' end of the special target, and no ligation reaction occurs. Mutations can be recognized in this way.

When the special target has normal nucleotides, the opposite reactions occur: ligation occurs for the normal probe, but for the mutant probe, because the special target does not have a deleted nucleotide, the nucleotide near the 3' end of the mutant probe does not match up with the nucleotide near the 5' end of the special target, and no ligation reaction occurs. Mutations can be recognized in this way.

Nucleotide insertion mutations are recognized according to the same principles: the mutant probe is longer by the length of the inserted nucleotide than the normal probe at the 3' end, and recognition and detection are based on the opposite pattern from that of nucleotide deletion mutations.

Figure 6:
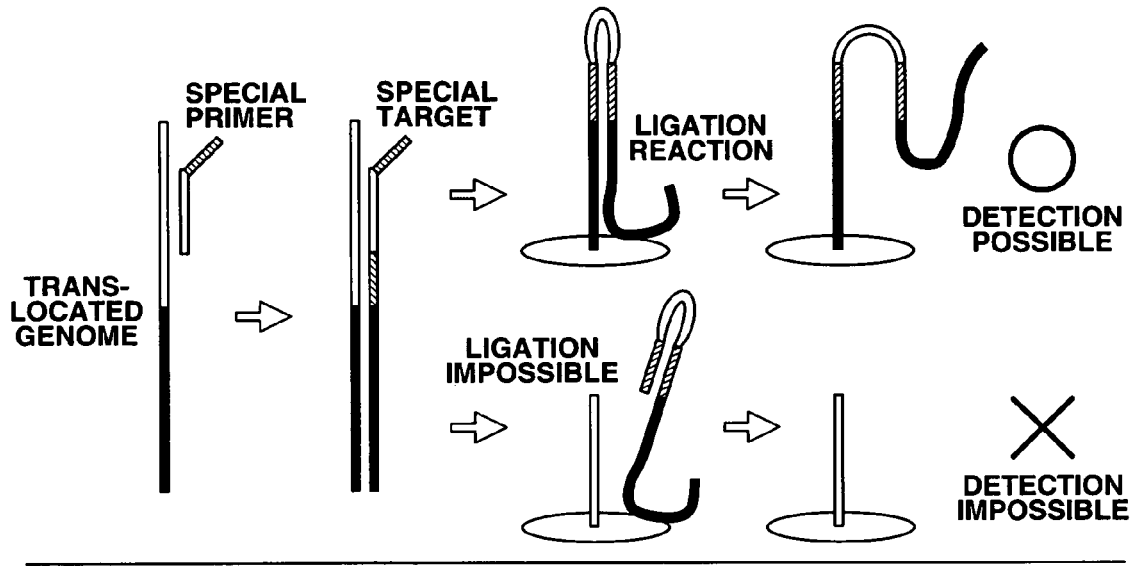
FIG. 6 is an explanatory drawing showing the analysis of translocation mutations according to the detection method of the present invention.
Figure 6:
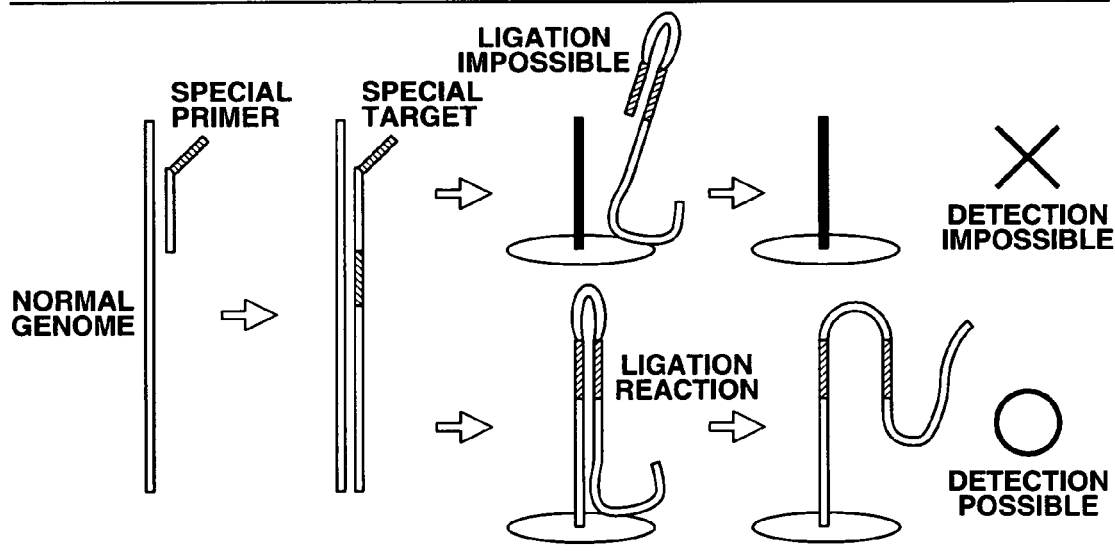
Figure 6:
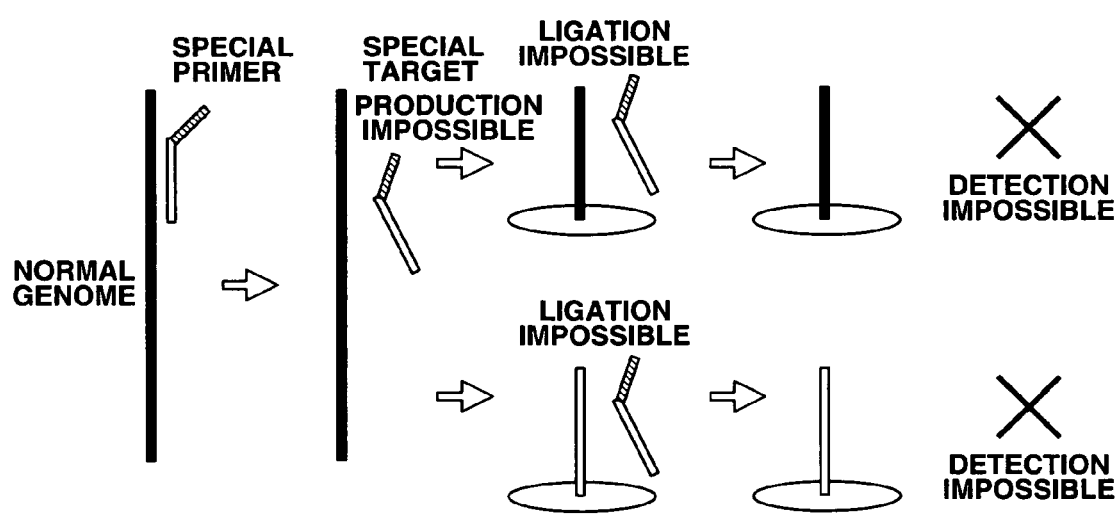

Analysis of translocation mutations according to the detection method of the present invention is explained with reference to FIG. 6.

When the special target has a translocation mutation, a ligation reaction occurs only with the mutant probe, resulting in joining of the special target. In this way, a greater signal for the probe is obtained than before ligation. For the normal probe, however, the probe lacks the region of hybridization with the special target, so hybridization does not occur, and there is no ligation reaction. Consequently, the signal the probe is the same as before the ligation. The presence or absence of translocation mutations can be recognized based on this difference of signal strength.

When a normal nucleotide sequence of no translocation is used as the template for forming the special target, the target hybridizes with the normal probe, and a ligation reaction occurs. For the mutant probe, no hybridization occurs, and therefore there is no ligation and no signal change appears. The circumstance in which the special primer cannot hybridize on the template can be ignored since the special target itself never forms and is not involved in the subsequent reactions, and no signal change appears with either the normal or mutant probe. Translocation mutations can be recognized in this way.

With the detection method of the present invention, detection is possible even at room temperature, and analytical measurements can be performed in a short amount of time.

With the detection method of the present invention, only two-step reaction is required after addition of the special target prepared as sample into the mutation detection reaction system.

Based on detection results from the method of the present invention, it is then possible to analyze correlations between genetics and phenotype in the fields of biology and medicine.

The detection method of the present invention is also applicable to the field of gene diagnosis when used to analyze specific genes for drug-metabolizing enzymes, tumor suppression factors and the like. It may also be useful in the prevention and the like of degenerative diseases such as cancer and high blood pressure.

[Detection System]

A detection chip, detection device or other detection system for nucleotide mutations using the aforementioned detection method for nucleotide mutations is provided by the present invention. Specific examples include a substrate or chip on which are collected a number of electrodes on which probes are fixed with one type of probe for a single electrode. Using these, it is possible to achieve simultaneous detection of multiple types of nucleotide mutations.

Because the detection system of the present invention uses the aforementioned detection method for nucleotide mutations, it is capable of determining and quantifying nucleotides at specific positions in a DNA, RNA or other nucleotide sequence, and can analyze a variety of mutations including single nucleotide polymorphism, short nucleotide tandem repeat mutations, nucleotide deletion mutations, nucleotide insertion mutations and translocation mutations rapidly and with high sensitivity.

The detection method and detection system for nucleotide mutations of the present invention were explained above using preferred embodiments thereof, but the present invention is not limited by these embodiments, and of course other embodiments exist.

In the aforementioned embodiments of the detection method of the present invention, electrodes are used as the base for the probes when fixed probes are used, but the base need not be an electrode, and glass (glass plate, glass beads or the like), resin (resin beads, membrane, thread or the like), gel or some other solid phase may also be used. When such a solid phase is used rather than electrodes, the linkage on glass or the like may be avidin-streptavidin or carboxyl group-amino group as in the case of a gold electrode, while in the case of a resin or gel, adhesion fixing can be achieved through physical properties even if the DNA lacks a reactive group. In the case of resin in particular strong fixing with DNA can be achieved with UV light radiation. Using such fixing methods, probes can be fixed on solid phases other than electrodes.

In addition to the electrochemical methods mentioned above, the detection method of the present invention allows for detection and quantification with a fluorescence detector using a fluorescent DNA dye (ethylene bromide or SYBR-Green (trade name)) or the like when detection is performed with a fixed probe. Detection and quantification are also possible using a method in which a fluorescent label is attached to the special probe in advance, or a method in which a substance (such as a fluorescence-emitting adapter substance) which emits light when it binds to a specific substance is attached to the DNA in advance.

If the probe is removed from the solid phase for measurement, it can for example be quantified by electrophoresis isolation. If there is a large amount of DNA to be detected, it can also be quantified by absorbance.

In this explanation, nucleotide mutations in the genome have been used as an example of subjects for detection, but other subjects of detection are possible in the detection method of the present invention, including for example nucleotide mutations in DNA, RNA and other nucleic acids.

The following is an embodiment of the detection method of the present invention using a method other than electrochemical detection.

1. Each special primer is labeled in advance with a fluorescent dye having a different emission wavelength.
2. PCR or A-PCR is performed with a sample genome and fluorescent labeled special primers, and counter-primers if it is necessary, and florescent labeled special targets are prepared.
3. Hybridization and ligation reactions are performed on the probes fixed in certain amounts on a solid phase with the fluorescent labeled special targets of 2.
4. After removal of nonspecific DNA, the special target from the ligation reaction is detected and quantified with a fluorescence detector.

Two embodiments of the detection method of the present invention carried out with an unfixed probe are given as (1) and (2) below. Detection with an unfixed probe is possible if the following process is followed.

(1)
1. A purification tag is attached to the probe.
2. Hybridization, ligation and other reactions are performed in a liquid phase.
3. Only the tagged DNA is purified in a column or the like.
4. The DNA is subjected to SDS-PAGE, and DNA longer than the original probe is detected and quantified.

(2)
1. Each probe is labeled in advance with a fluorescent dye having a different emission wavelength.
2. Hybridization, ligation and other reactions are performed in a liquid phase.
3. The reaction solution is subjected to SDS-PAGE, and fluorescence-emitting DNA longer than the fluorescent labeled probe is detected and quantified.

Figure 16:
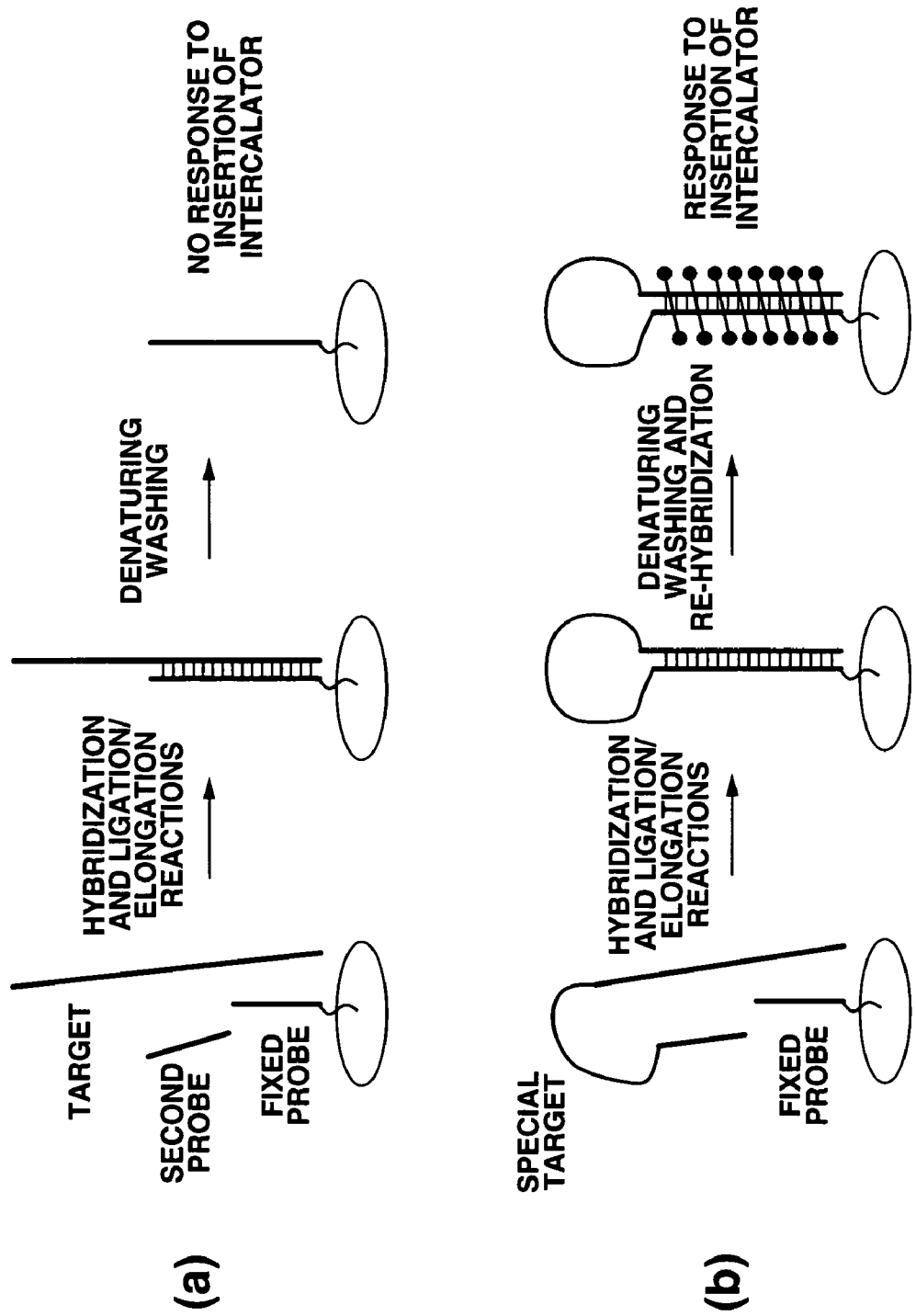
FIG. 16 is an explanatory drawing showing analysis using an intercalator.

The detection method of the present invention using an intercalator is explained in comparison with conventional detection methods with reference to FIG. 16.

As shown in FIG. 16($a$), in conventional detection methods using ligation, the target is first hybridized with a fixed probe, followed by a ligation reaction with a second probe. Ligation with the second probe results in elongation of the fixed probe, and the denaturing and washing process which removes non-specifically bound target and genome results in dissociation of the target, leaving only the elongated single-strand probe. Consequently, a double-strand specific intercalator (such as a fluorescent modified intercalator or electrochemical intercalator) cannot be used effectively for detection in conventional methods.

In contrast, using the detection method of the present invention, as shown in FIG. 16($b$), when the aforementioned special target is prepared and used in hybridization a loop is formed. Consequently, even if washing and denaturing are performed after the hybridization and ligation/elongation reactions, the special target itself remains joined to the fixed probe and is not washed away, so it can form a double strand if placed in an environment where it can again hybridize.

Thus, in the detection method of the present invention, highly effective detection is possible if a double-strand specific intercalator (such as a fluorescent modified intercalator or electrochemical intercalator) is used.

The method of detecting nucleotide mutations of the present invention offers the dramatic advantage of highly diverse detection systems.

EXAMPLES

The method of detecting nucleotide mutations of the present invention is explained in still more detail below using examples. However, the present invention is not in any way limited by these examples.

Example 1

(Detection of a Single Nucleotide Mutation)
(1) Using gold array electrodes (24 electrodes divided into groups A-F of four each), 1 μL of the normal probe described below with a concentration of 10 pmol/μL was placed on the electrode pin ends of groups A-C, 1 μL of the single nucleotide mutation probe described below with the same concentration was placed on the electrode pin ends of groups D-F, and fixing carried out.

Normal Probe:

i) Structure:
HS-(CH$_2$)$_6$-gaattagctgtatcgtcaaggcactcttgcctacgccacc ii) Oligonucletoide: Sequence length 40 nucleotides
iii) Electrode fixing part: thiol group
iv) Linker part: alkane chain with carbon number 6
v) Has normal nucleotide at the 3' end (C)

Single Nucleotide Mutation Probe:

i) Structure:
HS-(CH$_2$)$_6$-gaattagctgtatcgtcaaggcactcttgcctacgccacg ii) Oligonucleotide: sequence length 40 nucleotides
iii) Electrode fixing part: thiol group
iv) Linker part: alkane chain with carbon number 6
v) Has mutant nucleotide at the 3' end (G)

(2) The array electrodes were dipped and washed in a measurement electrolytic buffer (mixed buffer of potassium acetate and potassium chloride) containing no electrochemical reagents. This served to remove the non-specifically bound DNA.
(3) The first DPV measurement was performed at this stage to confirm the amount of probe fixed on the gold electrode surfaces. Namely, for the probe fixed on the gold electrodes (as single-strand DNA) the DPV response after fixing of the probe was measured (i1) using a double chain-specific electrochemical reagent solution.
(4) A reaction solution was prepared for the simultaneous hybridization and ligation reactions. The reaction solution contained T4 DNA ligase, 1× T4 DNA ligase buffer, only those salts required for hybridization, and 10 pmol/uL of each of the targets (normal, mixture of normal and single nucleotide mutation (5 pmol/uL each), single nucleotide mutation).

(Special Targets)
The special target of this oligo synthesis was constructed with the product obtained from an elongation reaction (enzyme elongation reaction, PCR reaction, A-PCR reaction) of genome DNA in mind.

Normal Special Target:

i) Structure:
(P)-agctccaactaccacggcctgctgaaaatgactgaatataaacttg tggtagttggagctggtggcgtaggcaagagtgc ii) Oligonucleotide: sequence length 80 nucleotides
iii) 5' end nucleotide: phosphoric acid group added
iv) 61$^{st}$ nucleotide from 5' end nucleotide is normal (G)
v) Sequence of 1$^{st}$-15$^{th}$ nucleotides from 5' end nucleotide is a special region to be added to the 5' end of the special primer.
vi) Sequence of 16$^{th}$-45$^{th}$ nucleotides from 5' end nucleotide is a loop-forming region (fold), and at the same time this region is the primer region (Tm setting about 85° C.) which hybridizes with genome DNA when constructing a special target from genome DNA.
vii) The 1$^{st}$-15$^{th}$ and 46$^{th}$-60$^{th}$ nucleotides from the 5' end nucleotide form complementary sequences when the loop is formed (Tm setting about 50° C.).
viii) Within the special target, the Tm setting for vi) is greater than that for vii), with a difference between the two of 25° C. or more.
ix) The nucleotide immediately downstream from the hybrid region formed in vii) on the special target is positioned so that it corresponds to the nucleotide site which causes the mutation.
x) There are 20 nucleotides downstream from the hybrid region formed in vii) on the special target, which is constructed so as to have a sequence of 20 nucleotides complementary to the probe (Tm about 66° C.).

Single Nucleotide Mutation Special Target:
Basically the same as the normal special target described above. The differences are as follows.

i) Structure:
(P)-agctccaactaccacggcctgctgaaaatgactgaatataaacttg tggtagttggagctcgtggcgtaggcaagagtgc ii) 61$^{th}$ nucleotide from 5' end nucleotide is normal (C)
(5) 1 uL of special target was applied to each electrode, with the normal special target applied electrodes A and D, a mixture of the normal and single nucleotide mutation special targets applied to electrodes B and E, and the single nucleotide mutation special target applied to electrodes C and F, and the hybridization and ligation reactions performed with the fixed probe. The reactions were performed for 2 hours at room temperature.
(6) Non-specifically bound DNA was removed by the same washing method used in (2) above.
(7) DPV response (i2) after the hybridization and ligation reactions was measured. (A high DPV is shown with the response value for the hybridized special target added to the response during probe fixing).
(8) In order to remove those of the special targets hybridized in (7) above which did not undergo ligation, a denaturant was added to the electrolytic buffer used in (2) above, and dip washing performed.
(9) DPV response measurements (i3) were performed for the ligation reaction. (Values lower than the response values after hybridization but higher than the response values for probe fixing are obtained).

Figure 8:
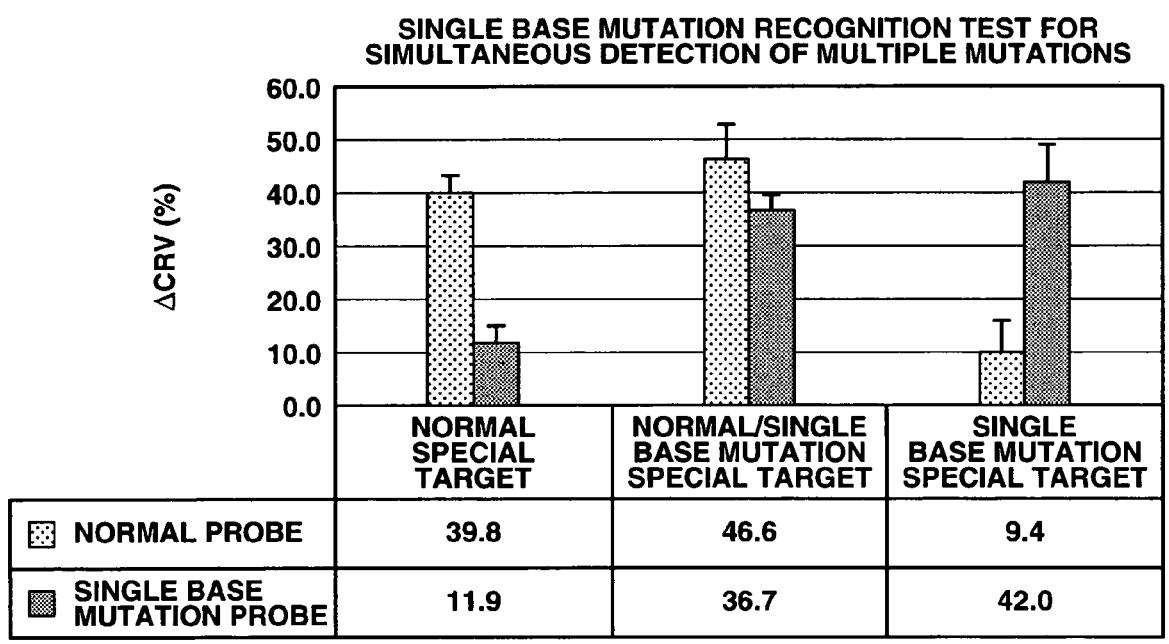
FIG. 8 is a graph showing measurement results for Example 1.

Results of the above measurements are shown in Table 1 and FIG. 8.

TABLE 1

| GROUP | i1 (nA) | i2 (nA) | i3 (nA) | ΔCRV (%) | | i1 (nA) | i2 (nA) | i3 (nA) | ΔCRV (%) |
|---|---|---|---|---|---|---|---|---|---|
| A | 1308 | 2746 | 1879 | 43.7 | MEAN | 1085.8 | 2233.0 | 1520.0 | 39.8 |
|   | 942 | 1986 | 1324 | 40.6 | STANDARD DEVIATION | 156.1 | 346.7 | 245.7 | 3.3 |
|   | 1045 | 2122 | 1455 | 39.2 | COEFFICIENT OF VARIATION | 14.4% | 15.5% | 16.2% | 8.3% |
|   | 1048 | 2078 | 1422 | 35.7 | | | | | |
| B | 890 | 1775 | 1280 | 43.8 | MEAN | 890.5 | 1799.8 | 1299.5 | 46.6 |
|   | 763 | 1612 | 1133 | 48.5 | STANDARD DEVIATION | 151.2 | 222.4 | 173.9 | 6.1 |
|   | 806 | 1694 | 1242 | 54.1 | COEFFICIENT OF VARIATION | 17.0% | 12.4% | 13.4% | 13.1% |
|   | 1103 | 2118 | 1543 | 39.9 | | | | | |
| C | 1311 | 2270 | 1328 | 1.3 | MEAN | 861.3 | 1518.5 | 929.0 | 9.4 |
|   | 790 | 1332 | 851 | 7.7 | STANDARD DEVIATION | 315.9 | 530.9 | 284.6 | 6.3 |
|   | 571 | 1028 | 654 | 14.5 | COEFFICIENT OF VARIATION | 36.7% | 35.0% | 30.6% | 66.4% |
|   | 773 | 1444 | 883 | 14.2 | | | | | |
| D | 796 | 1401 | 868 | 9.0 | MEAN | 755.8 | 1404.3 | 844.5 | 11.9 |
|   | 810 | 1475 | 889 | 9.8 | STANDARD DEVIATION | 62.0 | 82.8 | 46.9 | 3.2 |
|   | 744 | 1452 | 840 | 12.9 | COEFFICIENT OF VARIATION | 8.2% | 5.9% | 5.5% | 26.9% |
|   | 673 | 1289 | 781 | 16.0 | | | | | |
| E | 526 | 1094 | 725 | 37.8 | MEAN | 603.8 | 1210.3 | 821.0 | 36.7 |
|   | 510 | 1024 | 698 | 36.9 | STANDARD DEVIATION | 196.3 | 371.8 | 246.3 | 2.9 |
|   | 482 | 961 | 672 | 39.4 | COEFFICIENT OF VARIATION | 32.5% | 30.7% | 30.0% | 8.0% |
|   | 897 | 1762 | 1189 | 32.6 | | | | | |
| F | 633 | 1270 | 960 | 51.7 | MEAN | 563.5 | 1128.3 | 799.8 | 42.0 |
|   | 730 | 1439 | 987 | 35.2 | STANDARD DEVIATION | 155.0 | 288.8 | 219.1 | 6.9 |
|   | 522 | 1027 | 733 | 40.4 | COEFFICIENT OF VARIATION | 27.5% | 25.6% | 27.4% | 16.5% |
|   | 369 | 777 | 519 | 40.7 | | | | | |

NOTE:
ΔCRV SIGNIFIES COUPLING REACTION VALUE (FORMULA ΔCRV = i3 − i1/i1 × 100)

As shown in Table 1 and FIG. 8, when the normal probe was used there was a specific and obvious difference (normal 39.8%, single nucleotide mutation 9.4%) in the values for the ligation reactions of the normal and single nucleotide mutation special targets, and when the single nucleotide mutation probe was used there was also a specific and obvious difference (single nucleotide mutation 42.0%, normal 11.9%) in the ligation reactions of the aforementioned targets, indicating that homo-type single nucleotide mutations could be recognized. Moreover, looking at the values using both probes for the ligation reaction when a 1:1 mixture (heterotype) of both special targets was applied, the values were almost as high as they were when the targets were perfectly matched to the respective probes, which means that both probes underwent the ligation reaction and indicates that hetero-type mutations can also be distinguished. From this results it appears that this detection system is capable of distinguishing single nucleotide mutations of both homo and hetero types by applying both a single nucleotide mutation probe and a normal probe and comparing the values for the ligation reactions of the special targets.

Example 2

(Simultaneous Detection of Different Types of Mutations)

(1) Operations for fixing of the probes were the same as in Example 1. Namely, an array of gold electrodes (15 electrodes divided into groups A-C of 5 electrodes each) was used, with 1 µL of the normal probe described below applied to the pin ends of electrodes A at a concentration of 10 pmol/µL, 1 µL of the single nucleotide deletion probe described below applied to electrodes B at the same concentration, and 1 µL of the single nucleotide mutation probe described below applied to electrodes C at the same concentration, and fixing performed.

(Fixed Probes)

Normal Probe: the Same Oligo Probe Used in Example 1

Single Nucleotide Mutation Probe: the Same Oligo Probe Used in Example 1

Single Nucleotide Deletion Probe:

i) Structure;
HS-(CH$_2$)$_6$-tgaattagctgtatcgtcaaggcactcttgcctacgccac ii) Oligonucleotide: sequence length 40 nucleotides
iii) Electrode fixing part: thiol group
iv) Linker part: alkane group of carbon number 6
v) Designed so that the adjacent site one nucleotide downstream from the 3' end nucleotide matches the mutation site.

(2) Array electrodes were dipped and washed in a measurement electrolytic buffer (mixed buffer of potassium acetate and potassium chloride) containing no electrochemical reagents. This served to remove the non-specifically bound DNA.

(3) DPV response was measured (i1) following probe fixing.

(4) A reaction solution was prepared for simultaneously performing the hybridization and ligation reactions. The reaction solution contained T4 DNA ligase at a final concentration of 35 units/µL, 1× T4 DNA ligase buffer, only those salts required for hybridization, and 10 pmol/µL of the single nucleotide mutation special target (the same oligo single nucleotide mutation special target used in Example 1).

(5) 1 µL of the special target was applied to each of electrodes A-C, and hybridization and ligation reactions performed with the fixed probe. The reactions were performed for 2 hours at room temperature.

(6) In order to remove special target which had not undergone the ligation reaction, a denaturant was added to the electrolytic buffer used in (2) above, and dip washing performed.

(7) DPV response (i2) was measured for the ligation reaction.

Figure 9:
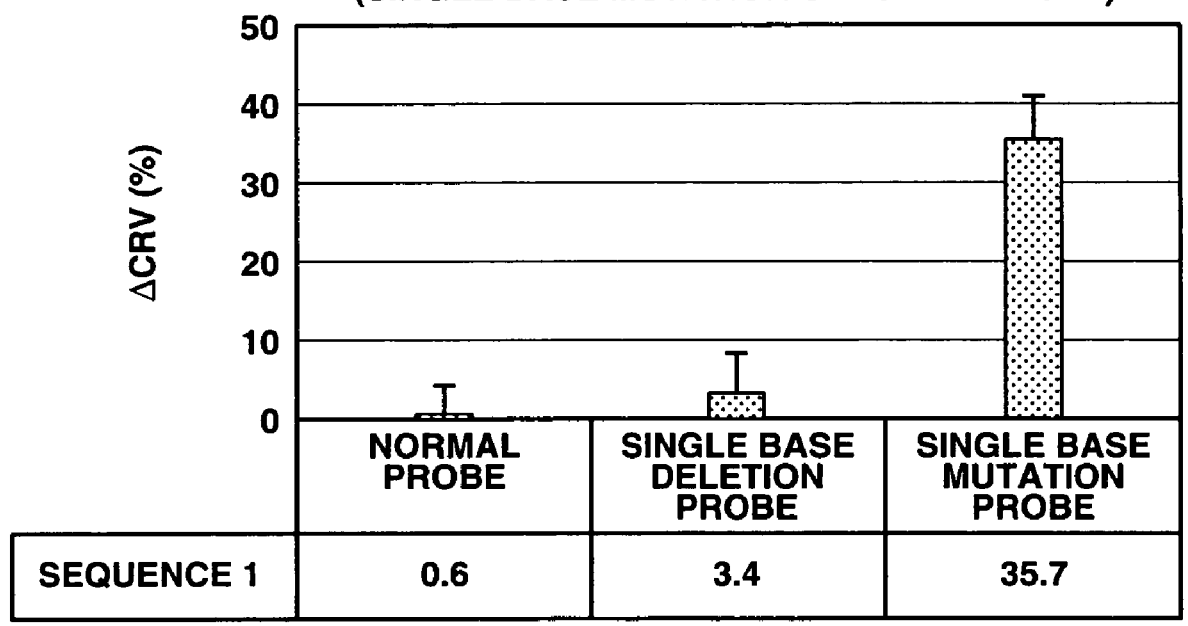
FIG. 9 is a graph showing measurement results for Example 2.

The results of the above measurements are shown in Table 2 and FIG. 9.

TABLE 2

| GROUP | i1 (nA) | i2 (nA) | ΔCRV (%) | | i1 (nA) | i2 (nA) | ΔCRV (%) |
|---|---|---|---|---|---|---|---|
| A | 688 | 678 | −1.5 | MEAN | 688.4 | 688.5 | 0.6 |
|   | 637 | 656 | 3.0 | STANDARD DEVIATION | 144.6 | 121.2 | 3.6 |
|   | 910 | 873 | −4.0 | COEFFICIENT OF VARIATION | 21.0% | 17.6% | 619.1% |
|   | 697 | 700 | 0.4 | | | | |
|   | 510 | 536 | 5.1 | | | | |
| B | 648 | 693 | 6.9 | MEAN | 590.4 | 610.5 | 3.4 |
|   | 500 | 537 | 7.3 | STANDARD DEVIATION | 77.0 | 88.9 | 5.1 |
|   | 683 | 721 | 5.5 | COEFFICIENT OF VARIATION | 13.0% | 14.6% | 151.5% |
|   | 591 | 562 | −5.0 | | | | |
|   | 530 | 541 | 2.0 | | | | |
| C | 926 | 1180 | 27.4 | MEAN | 797.6 | 1081.2 | 35.7 |
|   | 795 | 1103 | 38.8 | STANDARD DEVIATION | 122.4 | 157.0 | 5.3 |
|   | 611 | 818 | 33.9 | COEFFICIENT OF VARIATION | 15.3% | 14.5% | 14.7% |
|   | 770 | 1084 | 40.8 | | | | |
|   | 886 | 1220 | 37.7 | | | | |

NOTE:
ΔCRV SIGNIFIES COUPLING REACTION VALUE (FORMULA ΔCRV = i2 − i1/i1 × 100)

As shown in Table 2 and FIG. 9, with the normal probe, because one non-complementary nucleotide is present at the 3' end of the probe during hybridization with the single nucleotide mutation special target, ligation between the probe and the single nucleotide mutation special target does not occur at that site, and the ligation reaction value is only 0.6% (it is higher than 0% due to background noise). Even with the single nucleotide deletion probe, because the 3' end of the probe is lacking one nucleotide in comparison with the 5' end ligation site of the special target during hybridization with the single nucleotide mutation special target, no ligation reaction occurs, and the ligation reaction value is 3.4%—almost as low as for the aforementioned normal probe. With the single nucleotide mutation probe, on the other hand, the nucleotides are entirely complementary during hybridization with the single nucleotide mutation special target, so a good ligation reaction occurs, and a high ligation reaction value of 35.7% is achieved. From these results, it is clear that both non-complementariness and nucleotide deletion at the 3' end of the probe are recognized, and therefore different types of mutations can be detected simultaneously on the same electrode array.

Example 3

(Nucleotide Mutation Assay)
(1) The operation for fixing the probe was the same as in Example 1. Namely, gold array electrodes (15 electrodes in groups A-C of 5 electrodes each) were used, and 1 μL of a 10 pmol/μL single nucleotide mutation probe (the same oligo single nucleotide mutation probe used in Example 1) was applied to the pin tips of all the A-C electrodes, and fixing performed.
(2) The array electrodes were dipped and washed in a measurement electrolytic buffer (mixed buffer of potassium acetate and potassium chloride) containing no electrochemical reagents. This served to remove the non-specifically bound DNA.
(3) DPV response following probe fixing was measured (i1).
(4) A reaction solution was prepared for purposes of hybridization. The reaction solution contained final concentrations of 1× T4 DNA ligase buffer, only those salts required for hybridization, and 10 pmol/μL of each special target (normal, mixture of normal and single nucleotide mutation (5 pmol/μL each), single nucleotide mutation).
(5) 1 μL of the special targets was applied to the pins of electrodes A-C, and hybridization with the fixed probe performed for 1 hour at room temperature.
(6) The electrode pins were dip washed for 5 minutes at room temperature using the electrolytic buffer of (2) above. This step serves to remove any remaining unhybridized special target.
(7) A ligation reaction solution was prepared for purposes of the ligation reaction. The reaction solution contained a final concentration of 35 units/μL T4 ligase, 1× T4 DNA ligase buffer, and just enough salts so that the hybrid (2-strand) DNA formed by hybridization would not dissociate.
(8) 1 μL of the ligation reaction solution was applied to each of the electrodes in groups A-C, and ligation performed with the fixed probes. The reaction was performed for 1 hour at room temperature.
(9) In order to remove special target which had not undergone ligation, a denaturaant was added to the electrolytic buffer used in (2) above, and dip washing performed.
(10) DPV response (i2) was measured for the ligation reaction.

Figure 10:
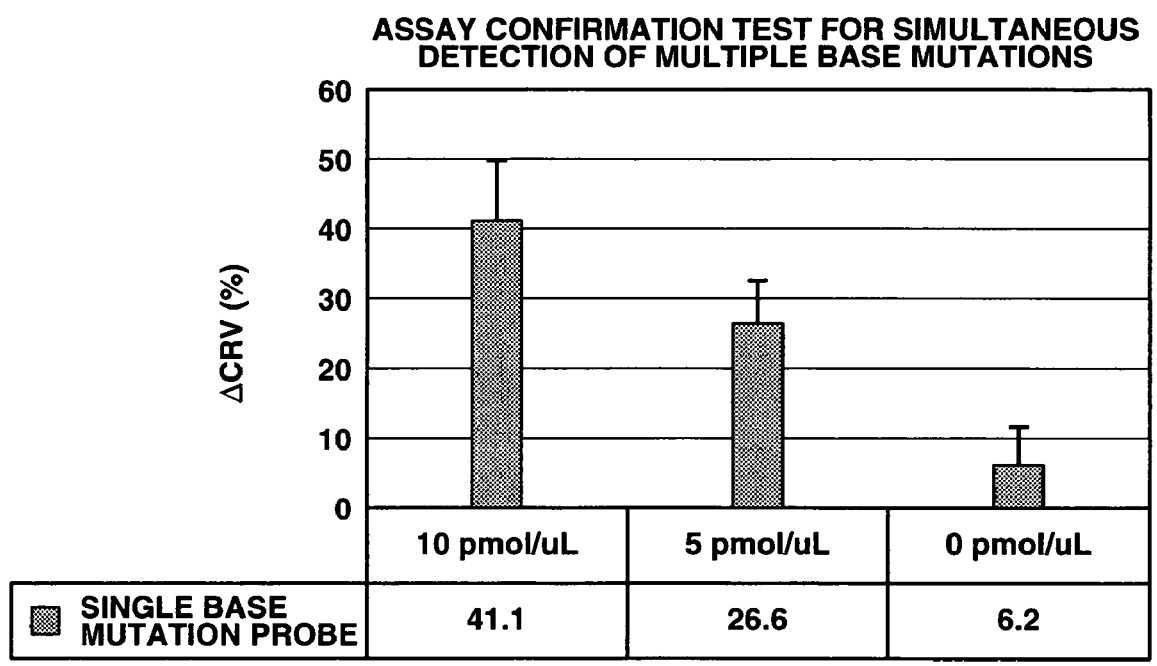
FIG. 10 is a graph showing measurement results for Example 3.

The results of the above measurements are given in Table 3 and FIG. 10.

TABLE 3

| GROUP | i1 (nA) | i2 (nA) | ΔCRV (%) | | i1 (nA) | i2 (nA) | ΔCRV (%) |
|---|---|---|---|---|---|---|---|
| A | 1201 | 1595 | 32.8 | MEAN | 710.0 | 988.8 | 41.1 |
|   | 575 | 875 | 52.2 | STANDARD DEVIATION | 329.3 | 409.9 | 8.5 |
|   | 569 | 776 | 36.4 | COEFFICIENT OF VARIATION | 46.4% | 41.5% | 20.7% |
|   | 495 | 709 | 43.2 | | | | |

TABLE 3-continued

| GROUP | i1 (nA) | i2 (nA) | ΔCRV (%) | | i1 (nA) | i2 (nA) | ΔCRV (%) |
|---|---|---|---|---|---|---|---|
| B | 1066 | 1407 | 32.0 | MEAN | 1129.8 | 1415.0 | 26.6 |
| | 596 | 783 | 31.4 | STANDARD DEVIATION | 404.7 | 461.2 | 5.9 |
| | 1538 | 1865 | 21.3 | COEFFICIENT OF VARIATION | 35.8% | 32.6% | 22.2% |
| | 1319 | 1605 | 21.7 | | | | |
| C | 1423 | 1476 | 3.7 | MEAN | 1366.0 | 1438.8 | 6.2 |
| | 1734 | 1734 | 0.0 | STANDARD DEVIATION | 288.4 | 230.6 | 5.5 |
| | 1052 | 1184 | 12.5 | COEFFICIENT OF VARIATION | 21.1% | 16.0% | 88.6% |
| | 1255 | 1361 | 8.4 | | | | |

NOTE:
ΔCRV SIGNIFIES COUPLING REACTION VALUE (FORMULA ΔCRV = i2 − i1/i1 × 100)

As shown in Table 3 and FIG. 10, using the single nucleotide mutation probe, when mutation detection measurements were performed using a single nucleotide mutation special target (10 pmol/µL), a mixture of single nucleotide mutation special target (5 pmol/µL) and normal special target (5 pmol/µL) and a normal target (10 pmol/µL), a ligation reaction value of 6.2% (noise response) was detected with the normal special target, which does not have the single nucleotide mutation special target. With the single nucleotide mutation special target, on the other hand, a high ligation reaction value of 41.1% was obtained, and a ligation response value of about half of that was obtained with the mixed special target. Subtracting the noise response factor, a positive correlation appears between these ligation reaction values and the detected target concentration, so it appears that this system has the ability to perform assay analysis.

Example 4

(Single Nucleotide Mutation Detection)
(1) The operations for fixing the probes were the same as in Example 1. Namely, gold array electrodes (24 electrodes in groups A-F of 4 electrodes each) were used, with 1 µL of the normal probe described below applied to each of the pin tips of electrodes A-C at a concentration of 10 pmol/µL, and 1 µL of the single nucleotide mutation probe described below applied to each of the electrodes D-F at the same concentration, and fixing was performed.

(Fixed Probes)

Normal Probe: the Same Oligo Probe Used in Example 1

Single Nucleotide Mutation Probe: the Same Oligo Probe Used in Example 1

(2) The DPV response after probe fixing was measured (i1)
(3) Three types of reaction solution (oligo special target, PCR special target, A-PCR special target) were prepared for purposes of the hybridization and ligation reactions, and the special target from oligo synthesis was applied to electrodes A and D, a special target (column purified) which was a PCR product prepared from a genome sample to electrodes B and E, and a special target (column purified) which was an A-PCR product prepared from a genome sample to electrodes C and F, each in the amount of 1 µL per electrode pin, and hybridization and ligation reactions performed with the fixed probes. The reaction solution was prepared from the various targets, T4 DNA ligase at a final concentration of 35 units µL, 1× T4 DNA ligase buffer and only those salts required for hybridization.

(Special Targets) 3 Types
   i) Oligo special target: same oligo target as in Example 1
   ii) Special target as PCR product:

```
Special primer:
agctccaactaccacggcctgctgaaaatgactgaatataaacttg
(46 mer)

Counter-primer:
ttctgaattagctgtatcgtcaag
(24 mer)
```

PCR was performed under the conditions described below with the 2 primers described above, using purified human genome DNA as the template.
   1. 95° C., 5 min
   2. 95° C., 30 sec
   3. 65° C., 30 sec
   4. 72° C., 15 sec
   5. 2.-4. repeated 30 times
   6. 0° C., 3 min The PCR product synthesized under these conditions was purified in a column and used as the PCR special target.
   iii) Special target as A-PCR product:

```
Special primer:
agctccaactaccacggcctgctgaaaatgactgaatataaacttg
(46 mer)
```

A-PCR was performed under the following conditions using this 1 type of special primer and the PCR product special target obtained in ii) as the template.
   1. 95° C., 5 min
   2. 95° C., 30 sec
   3. 70° C., 30 sec
   4. 72° C., 15 sec
   5. 2.-4. repeated 30 times
   6. 0° C., 3 min The A-PCR product synthesized under these conditions was purified in a column and used as the A-PCR special target.
(4) Residual reaction solution was removed.
(5) DPV response following hybridization and ligation reactions was measured (i2).

Figure 11:
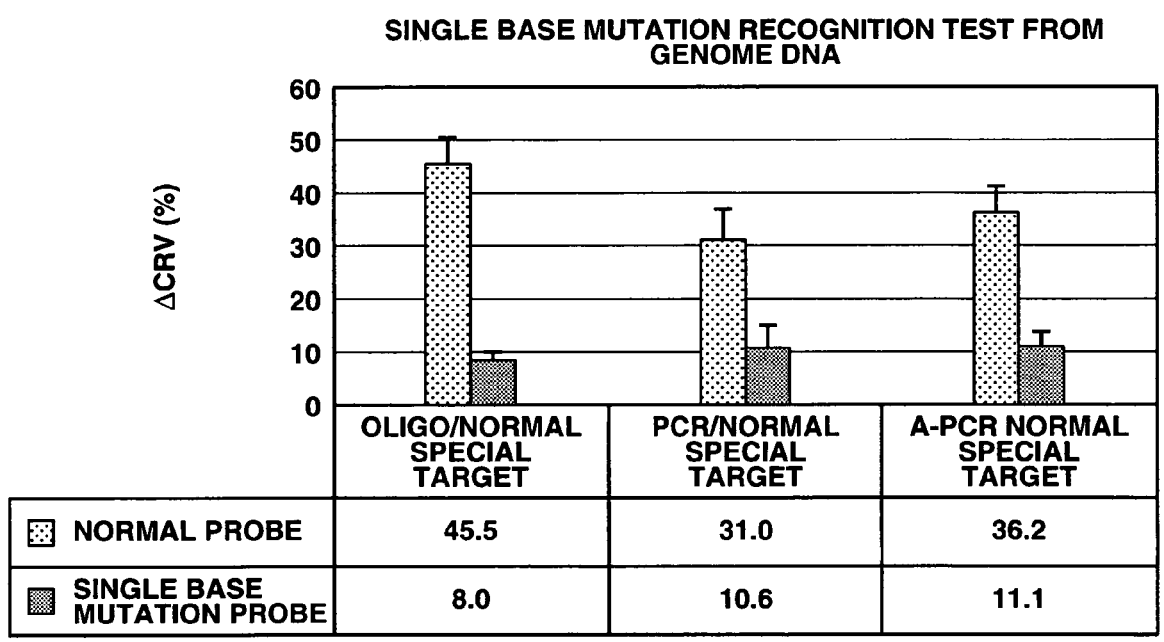
FIG. 11 is a graph showing measurement results for Example 4.

The results of the above measurements are shown in Table 4 and FIG. 11.

TABLE 4

| GROUP | i1 (nA) | i2 (nA) | ΔCRV (%) |  | i1 (nA) | i2 (nA) | ΔCRV (%) |
|---|---|---|---|---|---|---|---|
| A | 899 | 1279 | 42.3 | MEAN | 898.8 | 1303.0 | 45.5 |
|  | 770 | 1134 | 47.3 | STANDARD DEVIATION | 153.2 | 184.9 | 5.2 |
|  | 812 | 1234 | 52.0 | COEFFICIENT OF VARIATION | 17.0% | 14.2% | 11.4% |
|  | 1114 | 1565 | 40.5 |  |  |  |  |
| B | 912 | 1199 | 31.5 | MEAN | 974.3 | 1275.8 | 31.0 |
|  | 923 | 1276 | 38.2 | STANDARD DEVIATION | 85.5 | 111.3 | 5.8 |
|  | 1098 | 1433 | 30.5 | COEFFICIENT OF VARIATION | 8.8% | 8.7% | 18.8% |
|  | 964 | 1195 | 24.0 |  |  |  |  |
| C | 891 | 1187 | 33.2 | MEAN | 893.3 | 1213.3 | 36.2 |
|  | 763 | 1099 | 44.0 | STANDARD DEVIATION | 149.4 | 179.1 | 5.2 |
|  | 816 | 1093 | 33.9 | COEFFICIENT OF VARIATION | 16.7% | 14.8% | 14.4% |
|  | 1103 | 1474 | 33.6 |  |  |  |  |
| D | 786 | 856 | 8.9 | MEAN | 757.0 | 818.0 | 8.0 |
|  | 791 | 871 | 10.1 | STANDARD DEVIATION | 70.9 | 83.7 | 1.8 |
|  | 800 | 852 | 6.5 | COEFFICIENT OF VARIATION | 9.4% | 10.2% | 22.8% |
|  | 651 | 693 | 6.5 |  |  |  |  |
| E | 1254 | 1328 | 5.9 | MEAN | 849.8 | 932.8 | 10.6 |
|  | 789 | 852 | 8.0 | STANDARD DEVIATION | 285.5 | 282.2 | 4.4 |
|  | 582 | 660 | 13.4 | COEFFICIENT OF VARIATION | 33.6% | 30.3% | 41.2% |
|  | 774 | 891 | 15.1 |  |  |  |  |
| F | 1118 | 1246 | 11.4 | MEAN | 819.5 | 911.3 | 11.1 |
|  | 793 | 869 | 9.6 | STANDARD DEVIATION | 215.6 | 244.9 | 2.5 |
|  | 604 | 657 | 8.8 | COEFFICIENT OF VARIATION | 26.3% | 26.9% | 22.7% |
|  | 763 | 873 | 14.4 |  |  |  |  |

NOTE:
ΔCRV SIGNIFIES COUPLING REACTION VALUE (FORMULA ΔCRV = i2 − i1/i1 × 100)

As shown in Table 4 and FIG. 11, in a test of single nucleotide mutation identification in normal human genome, both the PCR product normal special target and A-PCR product normal special target exhibited a high response (PCR/31%, A-PCR/36.2%) with the normal probe, similar to results obtained for the oligo normal special target, while with the single-nucleotide mutation probe only a small response (PCR/10.6%, A-PCR/11.1%) was detected, similar to that detected with the oligo normal special target. These results show that with the detection method and detection system of the present invention identification of nucleotide mutations is good even using a PCR or A-PCR product, and that it is possible to detect nucleotide mutations using purified genome DNA as the initial sample.

Example 5

(Detection of a Single Nucleotide Mutation)
(1) Using gold array electrodes (24 electrodes divided into groups A-D of 6 electrodes each; 1 pin N as control), 2 μL of the following normal probe was applied to the pin tips of electrodes A and C at a concentration of 0.8 pmol/μL, while 2 μL of the following single nucleotide mutation probe was applied at the same concentration to the pin tips of electrodes B and D, and fixing performed.

(Fixed Probes)

Normal Probe i) Structure:

HS-$(CH_2)_6$-gttgtcctagcacctgacgcctcgttgtacatcagagacg ii) Oligonucleotide: Sequence length 40 nucleotides
iii) Electrode fixing part: thiol group
iv) Linker part: alkane chain of carbon number 6
v) Has normal nucleotide as the 3' end nucleotide (G)

Single Nucleotide Mutation Probe:

i) Structure:
HS-$(CH_2)_6$-gttgtcctagcacctgacgcctcgttgtacatcagagaca ii) Oligonucleotide: Sequence length 40 nucleotides
iii) Electrode fixing part: thiol group
iv) Linker part: alkane chain of carbon number 6
v) Has mutant nucleotide as the 3' end nucleotide (A)

(2) The array electrodes were dipped and washed in a denaturant. The array electrodes were then washed again in pure water. This served to remove non-specifically bound DNA.
(3) The first DPV measurements were taken at this stage to confirm the amount of probe fixed to the gold electrode surfaces. Namely, DPV response (i1) after probe fixing was measured for the probe fixed on the gold electrodes (as single-strand DNA), using a double-strand specific electrochemical reagent solution.
(4) A reaction solution was prepared for simultaneously performing the hybridization and ligation reactions. The reaction solution contained T4 DNA ligase, 1× T4 DNA ligase buffer, only those salts required for hybridization, and 10 pmol/μL of each target (10 pmol/μL each of the special target and conventional $1^{st}$ and $2^{nd}$ targets).

(Special Targets)
The special targets from oligo synthesis were constructed with the products obtained from an elongation reaction of genome DNA (enzyme elongation reaction, PCR reaction, A-PCR reaction) in mind.

Special Target:

i) Structure:
(P)-gagcattttacaccttgaagaccctccctttggaatggcacagggt acgtcttcaaggtgtaaaatgctccgtctctgatgtacaacgaggcgtca ggtgctaggaca ii) Oligonucleotide: sequence length 108 nucleotides iii) 5' end nucleotide: phosphoric acid group added iv) The nucleotide sequence 23-48 nucleotides from the 5' end is a loop-forming (folding) region v) The $1^{st}$-$22^{nd}$ and 49th-$70^{th}$ nucleotides from the 5' end are regions which become complementary sequences when the loop is formed vi) The $71^{st}$ nucleotide counting from the 5' end is downstream and immediately adjacent to the hybrid region formed in v) in the special target, and is located so as to correspond to the nucleotide site which causes the mutation (normal nucleotide is C)

vii) There are 38 nucleotides downstream from the hybrid region formed in v) on the special target, which is constructed so as to have a complementary sequence of 38 nucleotides with the probe.

Conventional $1^{st}$ and $2^{nd}$ Targets:

i) Structure (conventional $1^{st}$ target):

cctcccttcttggaatggcacagggtacgtcttcaaggtgtaaaatgctccg tctctgatgtacaacgaggcgtcaggtgctaggaca ii) Oligonucleotide: sequence length 86 nucleotides iii) The $49^{th}$ nucleotide counting from the 5' end is downstream and immediately adjacent to the hybrid region formed in v) in the special target, and is located so as to correspond to the nucleotide site which causes the mutation (normal nucleotide is C).

iv) The nucleotide sequence 1-26 nucleotides from the 5' end has the same nucleotides and the same length as the loop-forming (folding) region in the special target v) The $27^{th}$-$48^{th}$ Nucleotides from the 5' end and the second target are complementary sequences during hybridization and form a double strand.

vi) There are 38 nucleotides downstream from the hybrid region formed in v) on the special target, which is constructed to have a complementary sequence of 38 nucleotides with the probe.

i) Structure (conventional $2^{nd}$ target):

(P)-gagcattttacaccttgaagac ii) Oligonucleotide: sequence length 22 nucleotides iii) 5' end nucleotide: phosphoric acid group added iv) The $2^{nd}$ target and the $27^{th}$-$48^{th}$ nucleotides counting from the 5' end of the 1st target are regions of complementary sequences which form a double strand during hybridization.

(6) Using the special target for electrodes A and B and a mixture of the $1^{st}$ and $2^{nd}$ conventional targets for electrodes C and D, 1 μL of the target was applied to each electrode pin, and hybridization and ligation reactions performed with the fixed probe. Reactions were performed for 2 hours at room temperature.

(7) Non-specifically bound DNA was removed by the same washing methods used in (3) above.

(8) DVP response was measured (i2) for the hybridization and ligation reactions. (The response for the hybridized special target is added to the response for the fixed probe, producing a high DPV value.)

Figure 12:
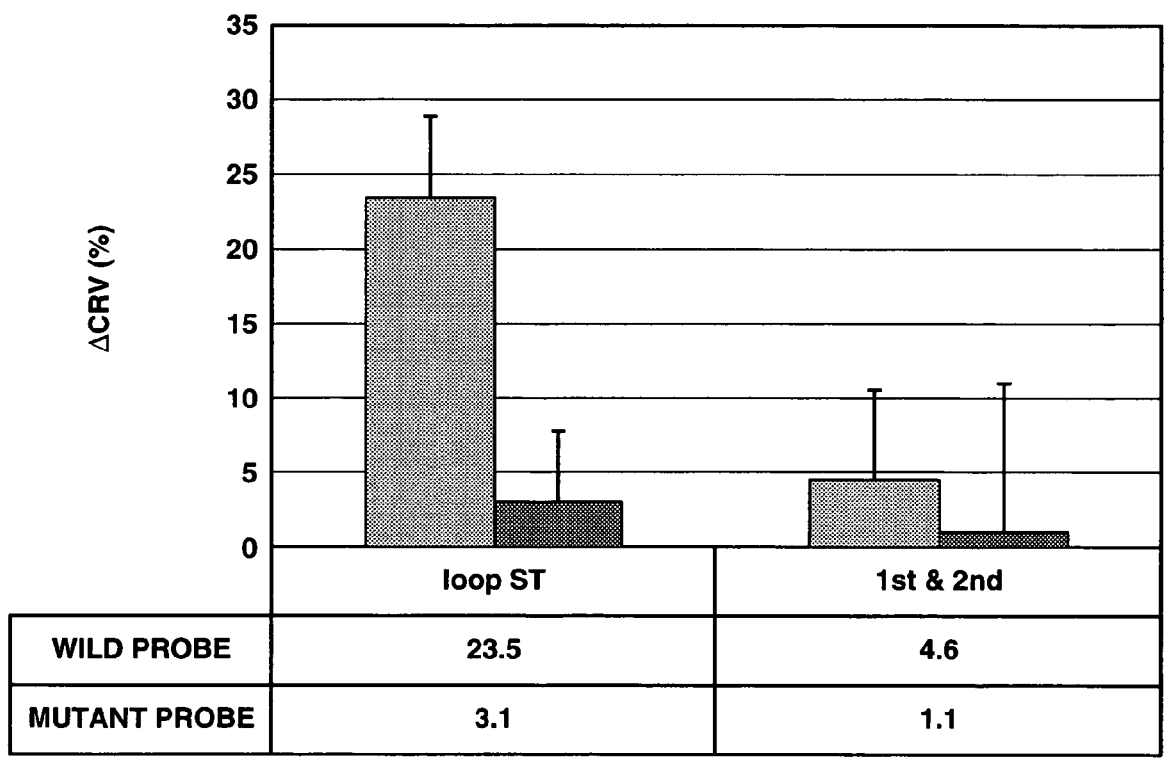
FIG. 12 is a graph showing measurement results for Example 5.

The results of the above measurements are shown in Table 5 and FIG. 12.

TABLE 5

| PIN No. | GROUP | | i1 (nA) | i2 (nA) | ΔCRV (%) |
|---|---|---|---|---|---|
| 1 | N | | | | −23.1 |
| 2 | A | MEAN | 477.8 | 589.7 | 23.5 |
| 3 | | STANDARD DEVIATION | 43.2 | 54.4 | 5.4 |
| 4 | | COEFFICIENT OF VARIATION | 0.1 | 0.1 | 0.2 |
| 5 | | | | | |
| 6 | | | | | |
| 7 | | | | | |
| 8 | B | MEAN | 393.3 | 405.5 | 3.1 |
| 9 | | STANDARD DEVIATION | 24.1 | 29.9 | 4.6 |
| 10 | | COEFFICIENT OF VARIATION | 0.1 | 0.1 | 1.5 |
| 11 | | | | | |
| 12 | | | | | |
| 13 | | | | | |
| 14 | C | MEAN | 433.5 | 454.5 | 4.6 |
| 15 | | STANDARD DEVIATION | 29.4 | 51.6 | 6.0 |
| 16 | | COEFFICIENT OF VARIATION | 0.1 | 0.1 | 1.3 |
| 17 | | | | | |
| 18 | | | | | |
| 19 | | | | | |
| 20 | D | MEAN | 296.8 | 294.8 | 1.1 |
| 21 | | STANDARD DEVIATION | 64.8 | 45.1 | 10.1 |
| 22 | | COEFFICIENT OF VARIATION | 0.2 | 0.2 | 9.3 |
| 23 | | | | | |
| 24 | | | | | |
| 25 | | | | | |

As shown in Table 5 and FIG. 12, using the special target, a specific and obvious significant difference (normal 20.5%, single nucleotide mutation 2.3%) was seen between the ligation reaction values for the normal and single nucleotide mutation probes, showing that the single nucleotide mutation was identified.

Using the conventional $1^{st}$ and $2^{nd}$ targets, on the other hand, the difference while significant was not particularly large (normal 9.1%, single nucleotide mutation 1.4%), so this method is not suited to detection with a double strand-specific intercalator. The responses for the conventional $1^{st}$ and $2^{nd}$ targets are probably attributable to single-strand non-specific binding of the intercalator. Therefore, the sensitivity of the detection method of the present invention is superior to that of conventional methods in analysis using a double-strand specific intercalator.

Example 6

(Single Nucleotide Mutation Detection)

(A) Preparation of Fluorescent Micro-Array Slides (1) A normal probe, hetero probe (1:1 mixture of normal and single nucleotide mutation probes) and single nucleotide mutation probe were spotted onto the surface of slide glass for purposes of fluorescent micro-array, and the 5' end amino group of the probe fixed to the glass surface. Spotting was performed using 25 μM of each probe solution, 11 spots per probe, forming round spots 200 μm in diameter.

Normal Probe:

i) Structure:

NH$_2$-gaatt agctg tatcg tcaag gcact cttgc ctacg ccacc ii) Oligonucleotide: sequence length 40 nucleotides iii) Glass surface fixing part: amino group iv) 3' end nucleotide is normal nucleotide (C)

Single Nucleotide Mutation Probe:

i) Structure:

NH$_2$-gaatt agctg tatcg tcaag gcact cttgc ctacg ccacg ii) Oligonucleotide: sequence length 40 nucleotides
  iii) Glass surface fixing part: amino group
  iv) 3' end nucleotide is mutant nucleotide (G)

(2) The micro-array slides were subjected to post-fixing treatment and washing. Namely, they were washed for 2 minutes with 0.2% SDS, washed twice in ultrapure water, washed for 5 minutes in 0.3N NaOH, washed twice in ultrapure water, boiled for 2 minutes in boiling ultrapure water, immersed for 3 minutes in chilled ethanol, and dried with compressed nitrogen gas.

(B) Preparation of Fluorescent-Labeled Special Target (3) The fluorescent-labeled special target used in the detection method of the present invention was prepared. Namely, PCR and Asymmetrical-PCR were performed using template DNA, special primer and counter-primer, aminoallyl dUTP was incorporated into the newly-synthesized oligo DNA, and a mutant target (fluorescent labeled special target) was prepared according to the aminoallyl method of coupling with the fluorescent material Cy3.

<Fluorescent Labeled Special Target>

Mutant Target:

i) Structure:

(P)-agctc caact accac ggcct gctga aaatg actga atata aactt gtggt agttg gagct cgtgg cgtag gcaag agtgc c ii) Oligonucleotide: sequence length 82 nucleotides, but with part of the T residue replaced by aminoallyl dUTP and fluorescent material Cy3 added to the aminoallyl
  iii) 5' end nucleotide: phosphoric acid group added
  iv) Nucleotide sequence 16$^{th}$-45$^{th}$ nucleotides from the 5' end is loop-forming (folding) region
  v) 1$^{st}$-15$^{th}$ and 46$^{th}$-60$^{th}$ nucleotides counting from the 5' end are regions that become complementary sequences when the loop is formed
  vi) The 61$^{th}$ nucleotide from the 5' end is downstream and immediately adjacent to the hybrid region formed in v) on the special target, and is positioned so as to correspond to the nucleotide site which causes the mutation (mutant nucleotide C)
  vii) There are 20 nucleotides downstream from the hybrid region formed in v) on the special target, which is constructed so as to have a sequence of 20 nucleotides complementary with the probe.

<Preparation of Fluorescent Labeled Special Target>

(4) The mutant special target was first prepared by PCR reaction using mutant template DNA, special primer and counter-primer. A reaction solution containing 1× Taq Buffer (for Hot Start), 250 μM of each dNTP, 1 pmol/μl special primer, 1 pmol/μl counter-primer, 0.2 pmol/μl template DNA and 0.05 unit/μl Taq polymerase was reacted for 2.5 minutes at 95° C. followed by 40 cycles of 30 seconds at 95° C., 30 seconds at 58° C. and 10 seconds at 72° C. Mutant template DNA i) Structure:

agctc caact accac ggcct gctga aaatg actga atata aactt gtggt agttg gagct cgtgg cgtag gcaag agtgc ii) Oligonucleotide: Sequence length 81 nucleotides
  iii) 5' end nucleotide: phopshoric acid group added Special primer:
  i) Structure: (P)-agctc caact accac ggcct gctga aaatg actga atata aacttg
  ii) Oligonucleotide: Sequence length 46 nucleotides
  iii) 5' end nucleotide: phosphoric acid group added Counter Primer:

i) Structure:

ggcac tcttg cctac gccac ii) Oligonucleotide: sequence length 20 nucleotides (5) Asymmetrical-PCR was performed using the PCR product and special primer obtained in (4) to obtain a target labeled with aminoallyl dUTP. A reaction solution containing 1× Taq Buffer (for Hot Start), 250 μM each of dGTP, dCTP and DATP, 150 μM dTTP, 100 μM aminoallyl dUTP, 1 pmol/μl special primer, 1/10 volume of PCR product and 0.05 unit/μl Taq polymerase was reacted for 2.5 minutes at 95° C. followed by 40 cycles of 30 seconds at 95° C., 30 seconds at 68.4° C. and 10 seconds at 72° C.

(6) The fluorescent material Cy3 was coupled to the aminoallyl dUTP-labeled target obtained in (5). Namely, Asymmetrical-PCR product which had been desalted and concentrated in a Microcon-10 column was dried in a speed vac, re-dissolved in 0.1M NaHCO$_3$ Buffer (pH 9.0), and mixed with Cy3 which had been dissolved in DMSO and dried in a speed vac, and a Cy3 incorporation reaction performed for 1 hour at room temperature. After the reaction 4M Hydroxylamine was added, the Cy3 was inactivated for 15 minutes at room temperature, and the unreacted dNTP and inactivated Cy3 were removed in a Microcon-10 column and a fluorescent labeled special target produced by concentration.

(C) Hybridization and Ligation Reactions (7) A reaction solution was prepared for simultaneously performing the hybridization and ligation reactions. The reaction solution contained T4 DNA ligase at a final concentration of 35 units/μL, 1× T4 DNA ligase buffer, only those salts required for hybridization, and 0.7 times volume of the fluorescent labeled special target.

(8) Cover glass was laid over the spots on the micro-array slides, the reaction liquid of (7) was poured in the gaps, and hybridization and ligation reactions were performed with the fixed probe. The reactions were performed for 2 hours at room temperature.

(9) Following removal of the cover glass in pure water, the slides were washed in flowing ultrapure water, dried with N$_2$ gas and dip washed for 10 minutes in 0.1M NaOH 1.5M KCl to remove the non-specifically bound DNA. They were then again washed in flowing ultrapure water, dried with N$_2$ gas and subjected to array analysis.

(10) The micro-array slides were scanned using a GenePix 2505B micro-array scanner to obtain scan images which were converted to numbers with a GenePix Pro.

(11) (Signal median —background median) was calculated from the numerical data, and mean and standard deviation calculated and used as the test results. (Results show the fluorescent strength of fluorescent-labeled special target ligated to the fixed probe.)

Figure 13:
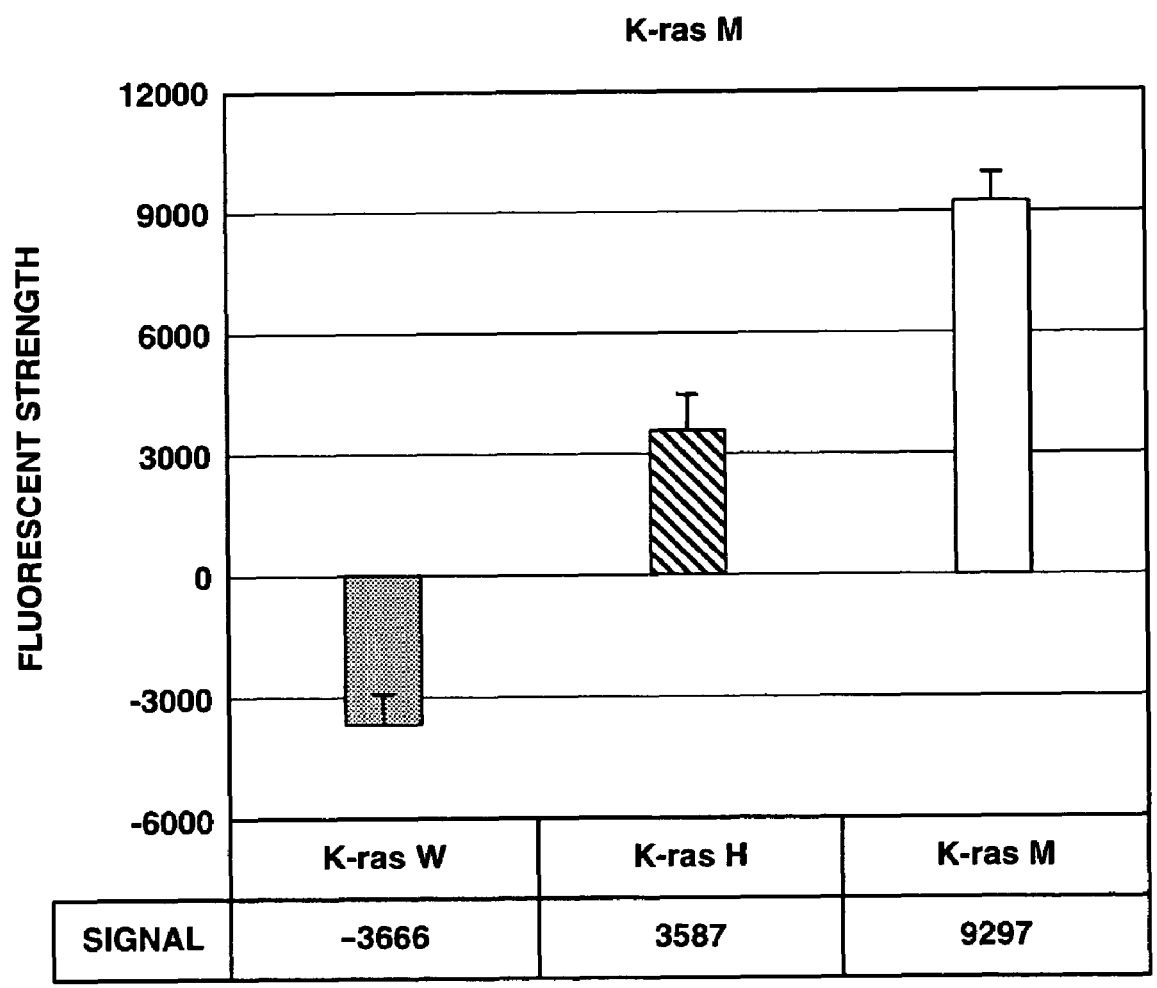
FIG. 13 is a graph showing measurement results for Example 6.

The results of the above measurements are shown in Table 6 and FIG. 13.

As shown in Table 6 and FIG. 13, specific and strong fluorescence was measured from the spots of the single nucleotide mutation K-ras M probe, which was completely complementary to the mutant target, while the fluorescence observed from the normal probe K-ras W spots was below background levels. This shows that the detection method of the present invention can detect single nucleotide mutations even when analysis is with fluorescent micro-array slides. The fluorescence values for the K-ras H hetero probe fell roughly between those of the normal and single nucleotide mutation probes, which indicates that the method is effective even in hetero analysis.

TABLE 6

| DETECTION PROBE TYPE | MEAN FLUORESCENCE STRENGTH | STANDARD DEVIATION |
| --- | --- | --- |
| K-ras W | −3666 | 723 |
| K-ras H | 3587 | 859 |
| K-ras M | 9297 | 680 |

EXPLANATION OF PROBES:
K-ras W: NORMAL GENE DETECTION PROBE
K-ras H: HETERO MUTATION GENE DETECTION PROBE
K-ras M: HOMO MUTATION GENE DETECTION PROBE Example 7

(Single Nucleotide Deletion Detection)

(A) Preparation of Fluorescent Micro-Array Slides (1) A normal probe, hetero probe (1:1 mixture of normal and single nucleotide deletion probes) and single nucleotide deletion probe were spotted onto the surface of slide glass for purposes of fluorescent micro-array, and the 5' end amino group of the probe fixed to the glass surface. Spotting was performed using 25 μM of each probe solution, 11 spots per probe, forming round spots 200 μm in diameter.

Normal Probe:

i) Structure:

$NH_2$-tggaggtacttttcagccaggatgtaacattggagaag ii) oligonucleotide: sequence length 38 nucleotides
iii) Glass surface fixing part: amino group
iv) 3' end nucleotide is normal nucleotide (G)

Single Nucleotide Deletion Probe:

i) Structure:

$NH_2$-atggaggtacttttcagccaggatgtaacattggagaa ii) Oligonucleotide: sequence length 38 nucleotides
iii) Glass surface fixing part: amino group
iv) 3' end has one nucleotide missing from the normal probe (2) The micro-array slides were subjected to post-fixing treatment and washing. Namely, they were washed for 2 minutes with 0.2% SDS, washed twice in ultrapure water, washed for 5 minutes in 0.3N NaOH, washed twice in ultrapure water, boiled for 2 minutes in boiling ultrapure water, immersed for 3 minutes in chilled ethanol, and dried with compressed nitrogen gas.

(B) Preparation of Fluorescent-Labeled Special Target (3) The fluorescent-labeled special target used in the detection method of the present invention was prepared. Namely, PCR and Asymmetrical-PCR were performed using template DNA, special primer and counter-primer, aminoallyl dUTP was incorporated into the newly-synthesized oligo DNA, and a normal target (fluorescent labeled special target) was prepared according to the aminoallyl method of coupling with the fluorescent material Cy3.

<Fluorescent Labeled Special Target>

Normal Target:

i) Structure:

(P)-ctatc cgcgt gattg cctaa ataat attta cctcc aagtc ctctc tctgc aatca cgcgg atagc ttctc caatg ttaca tcctg gc ii) Oligonucleotide: sequence length 87 nucleotides, but part of the T residue is replaced by aminoallyl dUTP, and fluorescent material Cy3 is added to the aminoallyl iii) 5' end nucleotide: phosphoric acid group added iv) Sequence of $17^{th}$-$48^{th}$ nucleotides from the 5' end are loop-forming (folding) region v) $1^{st}$-$16^{th}$ and $49^{th}$-$64^{th}$ nucleotides counting from the 5' end are regions which become complementary sequences when the loop is formed vi) the $65^{th}$ nucleotide from the 5' end is downstream and immediately adjacent to the hybrid region formed in v) in the special target, and is located so as to correspond to the nucleotide site which causes the mutation (normal nucleotide is C), vii) There are 22 nucleotides downstream from the hybrid region formed in v) on the special target, which is constructed to have a complementary sequence of 22 nucleotides with the probe.

<Preparation of Fluorescent Labeled Special Target>

(4) The normal target was first prepared by PCR reaction using the respective normal template DNA, special primer and counter-primer. A reaction solution containing 1× Taq Buffer (for Hot Start), 250 μM of each dNTP, 1 pmol/μl special primer, 1 pmol/μl counter-primer, 0.2 pmol/μl template DNA, and 0.05 unit/μl Taq polymerase was reacted for 2.5 minutes at 95° C. followed by 40 cycles of 30 seconds at 95° C., 30 seconds at 58° C. and 10 seconds at 72° C.

Normal Template DNA:

i) Structure: ctatc cgcgt gattg cctaa ataat attta cctcc aagtc ctctc tctgc aatca cgcgg atagc ttctc caatg ttaca tcctg gc ii) Oligonucleotide: sequence length 87 nucleotides
iii) 5' end nucleotide: phosphoric acid group added Special Primer:

i) Structure:- ctatc cgcgt gattg cctaa ataat attta cctcc aagtc ctctc tct ii) Oligonucleotide: sequence length 48 nucleotides iii) 5' end nucleotide: phosphoric acid group added Counter Primer:

i) Structure:

gccag gatgt aacat tggag aa ii) Oligonucleotide: sequence length 22 nucleotides (5) An aminoallyl dUTP-labeled target was obtained by Asymmetrical-PCR using the special primer and PCR product obtained in (4). A reaction solution containing 1× Taq Buffer (for Hot Start), 250 µM each of dGTP, dCTP and dATP, 150 µM dTTP, 100 µM aminoallyl dUTP, 1 pmol/µl special primer, 1/10 volume of PCR product and 0.05 unit/µl Taq polymerase was reacted for 2.5 minutes at 95° C. followed by 40 cycles of 30 seconds at 95° C., 30 seconds at 70° C. and 10 seconds at 72° C.

(6) The fluorescent material Cy3 was coupled to the aminoallyl dUTP-labeled target obtained in (5). Namely, Asymmetrical-PCR product which had been desalted and concentrated in a Microcon-10 column was dried in a speed vac, re-dissolved in 0.1M NaHCO$_3$ Buffer (pH 9.0), and mixed with Cy3 which had been dissolved in DMSO and dried in a speed vac, and a Cy3 incorporation reaction performed for 1 hour at room temperature. After the reaction 4M Hydroxylamine was added, the Cy3 was inactivated for 15 minutes at room temperature, and the unreacted dNTP and inactivated Cy3 were removed in a Microcon-10 column and a fluorescent labeled special target produced by concentration.

(C) Hybridization and Ligation Reactions (7) A reaction solution was prepared for simultaneously performing the hybridization and ligation reactions. The reaction solution contained T4 DNA ligase at a final concentration of 35 units/µL, 1× T4 DNA ligase buffer, salts, and 0.7 times volume of the fluorescent labeled special target.

(8) Cover glass was laid over the spots on the micro-array slides, the reaction liquid of (7) was poured into the gaps, and hybridization and ligation reactions were performed with the fixed probe. The reactions were performed for 2 hours at room temperature.

(9) Following removal of the cover glass in pure water, the slides were washed in flowing ultrapure water, dried with N$_2$ gas and dip washed for 10 minutes in 0.1M NaOH 1.5M KCl to remove the non-specifically bound DNA. They were then again washed in flowing ultrapure water, dried with N$_2$ gas and subjected to array analysis.

(10) The micro-array slides were scanned using a GenePix 2505B micro-array scanner to obtain scan images which were converted to numerical data with a GenePix Pro.

(11) (Signal median—background median) was calculated from the numerical data, and mean and standard deviation calculated and used as the test results. (Results show the fluorescent strength of fluorescent-labeled special target ligated to the fixed probe.)

Figure 14:
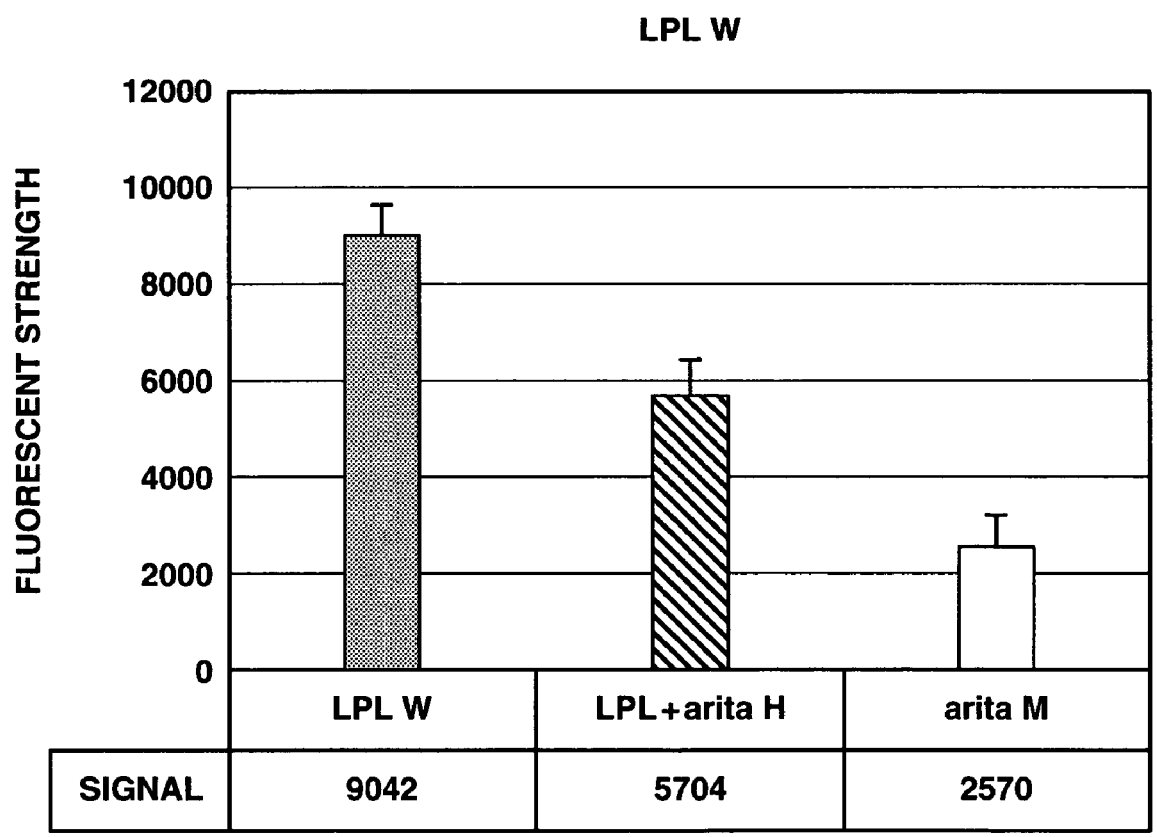
FIG. 14 is a graph showing measurement results for Example 7.

The results of the above measurements are shown in Table 7 and FIG. 14.

TABLE 7

| DETECTION PROBE TYPE | MEAN FLUORESCENT STRENGTH | STANDARD DEVIATION |
|---|---|---|
| LPL W | 9042 | 664 |
| LPL + arita H | 5704 | 761 |
| arita M | 2570 | 670 |

EXPLANATION OF PROBES:
LPL W: NORMAL GENE DETECTION PROBE
LPL + arita H: HETERO MUTANT GENE DETECTION PROBE
arita M: HOMO MUTANT GENE DETECTION PROBE As shown in Table 7 and FIG. 14, specific and strong fluorescence was measured from the spots of normal LPL W probe, which was completely complementary to the normal target, while the fluorescence observed from the single nucleotide deletion arita M probe spots was comparatively weak. This shows that the detection method of the present invention can detect single nucleotide deletions even when analysis is with fluorescent micro-array slides. The fluorescence values for the LPL+arita H hetero probe fell roughly between those of the normal and single nucleotide mutation probes, which indicates that the method is effective even in hetero analysis, thus supporting the superiority of the detection method of the present invention.

Example 8

(Translocation Detection)

(A) Preparation of Fluorescent Micro-Array Slides (1) Translocation detection and normal probes were spotted onto slide glass for purposes of fluorescent micro-array, and the amino groups at the 5' ends of the probes were fixed to the glass. Spotting was performed using 25 µM of each probe solution, 11 spots per probe, forming round spots 200 µm in diameter.

Translocation Detection Probe:

i) Structure:

NH$_2$-catcg tccac tcagc cactg gattt aagca gagtt caa ii) Oligonucleotide: sequence length 38 nucleotides iii) Glass surface fixing part: amino group iv) BCR nucleotide sequence with 3' end immediately upstream from BCRABL translocation spot Normal Probe:

i) Structure:

NH$_2$-gaagg ggctg tcctc gtcct ccagc tgtta tctgg aag ii) Oligonucleotide: Sequence length 38 nucleotides iii) Glass surface fixing part: amino group iv) ABL nucleotide sequence with the 3' end immediately upstream from BCRABL translocation spot in the normal ABL nucleotide sequence (2) The micro-array slides were subjected to post-fixing treatment and washing. Namely, they were washed for 2 minutes with 0.2% SDS, washed twice in ultrapure water, washed for 5 minutes in 0.3N NaOH, washed twice in ultrapure water, boiled for 2 minutes in boiling ultrapure water, immersed for 3 minutes in chilled ethanol, and dried with compressed nitrogen gas.

(B) Preparation of Fluorescent-Labeled Special Target (3) The fluorescent-labeled special target used in the detection method of the present invention was prepared. Namely, PCR and Asymmetrical-PCR were performed using template DNA, special primer and counter-primer, aminoallyl dUTP was incorporated into the newly-synthesized oligo DNA, and a translocated target (fluorescent labeled special target) was prepared according to the aminoallyl method of coupling with the fluorescent material Cy3.

<Fluorescent Labeled Special Target>

Translocated Target:

i) Structure:
(P)-aagcc cttca gcggc cctga ggctc aaagt cagat gctac tggcc tctga agggc ttttg aactc tgctt aaatc cagtg ii) Oligonucleotide: sequence length 80 nucleotides, but with part of T residue replaced by aminoallyl dUTP, and fluorescent material Cy3 added to the aminoallyl iii) 5' end nucleotide: phosphoric acid group added iv) The nucleotide sequence of $17^{th}$-$41^{st}$ nucleotides from the 5' end is a loop-forming (folding) region v) The $1^{st}$-$16^{th}$ and $42^{nd}$-$57^{th}$ nucleotides counting from the 5' end are regions which become complementary sequences when the loop is formed vi) The $58^{th}$ nucleotide from the 5' end is downstream and immediately adjacent to the hybrid region formed in v) in the special target, and is located so as to correspond to the nucleotide site which causes the translocation (nucleotide of translocated form is T)

vii) There are 22 nucleotides downstream from the hybrid region formed in v) on the special target, which is constructed to have a sequence of 22 nucleotides complementary to the translocation detection probe.

<Preparation of Fluorescent Labeled Special Target>

(4) The translocated special target was first prepared by PCR reaction using translocated template DNA, special primer and counter-primer. A reaction solution containing 1× Taq Buffer (for Hot Start), 250 μM of each dNTP, 1 pmol/μl special primer, 1 pmol/μl counter-primer, 0.2 pmol/μl template DNA, and 0.05 unit/μl Taq polymerase was reacted for 2.5 minutes at 95° C. followed by 40 cycles of 30 seconds at 95° C., 30 seconds at 58° C. and 10 seconds at 72° C. Translocated template DNA i) Structure:
aagcc cttca gcggc cctga ggctc aaagt cagat gctac tggcc tctga agggc ttttg aactc tgctt aaatc cagtg gctga gtgga cgatg acatt cagaa accca tagag cc ii) Oligonucleotide: sequence length 117 nucleotides iii) 5' end nucleotide: phosphoric acid group added Special Primer:

i) Structure:-
aagcc cttca gcggc cctga ggctc aaagt cagat gctac tg ii) Oligonucleotide: sequence length 42 nucleotides iii) 5' end nucleotide: phosphoric acid group added Counter-Primer:

i) Structure:

cactg gattt aagca gagtt ca ii) Oligonucleotide: sequence length 22 nucleotides (5) Asymmetrical-PCR was performed using the PCR product and special primer obtained in (4) to obtain a target labeled with aminoallyl dUTP. A reaction solution containing 1× Taq Buffer (for Hot Start), 250 μM each of dGTP, dCTP and DATP, 150 μM dTTP, 100 μM aminoallyl dUTP, 1 pmol/μl special primer, 1/10 volume of PCR product and 0.05 unit/μl Taq polymerase was reacted for 2.5 minutes at 95° C. followed by 40 cycles of 30 seconds at 95° C., 30 seconds at 70° C. and 10 seconds at 72° C.

(6) The fluorescent material Cy3 was coupled to the aminoallyl dUTP-labeled target obtained in (5). Namely, Asymmetrical-PCR product which had been desalted and concentrated in a Microcon-10 column was dried in a speed vac, re-dissolved in 0.1M NaHCO$_3$ Buffer (pH 9.0), and mixed with Cy3 which had been dissolved in DMSO and dried in a speed vac, and a Cy3 incorporation reaction performed for 1 hour at room temperature. After the reaction 4M Hydroxylamine was added, the Cy3 was inactivated for 15 minutes at room temperature, and the unreacted dNTP and inactivated Cy3 were removed in a Microcon-10 column and a fluorescent labeled special target produced by concentration.

(C) Hybridization and Ligation Reactions (7) A reaction solution was prepared for simultaneously performing the hybridization and ligation reactions. The reaction solution contained T4 DNA ligase at a final concentration of 35 units/μL, 1× T4 DNA ligase buffer, salts, and 0.7 times volume of the fluorescent labeled special buffer.

(8) Cover glass was laid over the spots on the micro-array slides, the reaction liquid of (7) was poured in the gaps, and hybridization and ligation reactions were performed with the fixed probe. The reactions were performed for 2 hours at room temeprature.

(9) Following removal of the cover glass in pure water, the slides were washed in running ultrapure water, dried with N$_2$ gas and dip washed for 10 minutes in 0.1M NaOH 1.5M KCl to remove the non-specifically bound DNA. They were then again washed in running ultrapure water, dried with N$_2$ gas and subjected to array analysis.

(10) The micro-array slides were scanned using a GenePix 2505B micro-array scanner to obtain scan images which were converted to numerical data with a GenePix Pro.

(11) (Signal median—background median) was calculated from the numerical data, and mean and standard deviation calculated and used as the test results. (Results show the fluorescent strength of fluorescent-labeled special target ligated to the fixed probe.)

Figure 15:
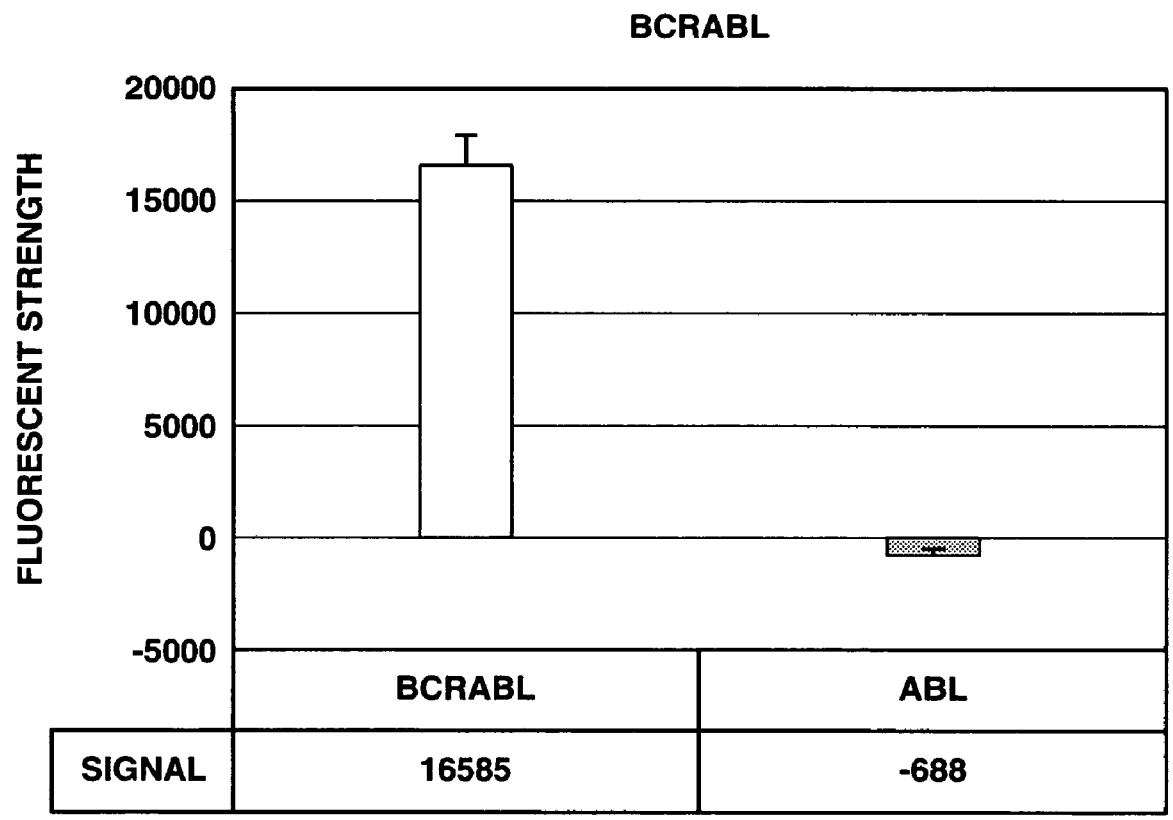
FIG. 15 is a graph showing measurement results for Example 8.

The results of the above measurements are shown in Table 8 and FIG. 15.

TABLE 8

| DETECTION PROBE TYPE | MEAN FLUORESCENT STRENGTH | STANDARD DEVIATION |
| --- | --- | --- |
| BCRABL | 16585 | 1364 |
| ABL | −688 | 202 |

EXPLANATION OF PROBES:
BCRABL: TRANSLOCATION MUTATION DETECTION PROBE
ABL: NORMAL ABL GENE DETECTION PROBE

As shown in Table 8 and FIG. 15, specific and strong fluorescence was measured from the spots of the BCRABL translocation detection probe, which was completely complementary to the translocated target, while the fluorescence observed from the normal ABL probe spots hardly exceeded background levels. This shows that the detection method of the present invention can detect translocations even when analysis is with fluorescent micro-array slides.

INDUSTRIAL APPLICABILITY

With the detection method of the present invention it is possible to detect and assay nucleotides at specific locations in a DNA, RNA or other nucleotide sequence, and to rapidly analyze a variety of nucleotide mutations including single nucleotide mutations, multiple nucleotide mutations, nucleotide deletion mutations, nucleotide insertion mutations and translocation mutations.

---

The invention claimed is:

1. A method of detecting a mutation in a polynucleotide, wherein the mutation is selected from the group consisting of single nucleotide polymorphisms, short nucleotide tandem repeat mutations, nucleotide deletion mutations, nucleotide insertion mutations, and translocations, said method comprising:

producing an elongatable-primer and a counter-primer,
wherein the elongatable-primer has (1) a nucleotide sequence A complementary to a portion of said polynucleotide, which portion is 3' of the mutation to be detected, and (2) a nucleotide sequence B' added to the 5' end of sequence A, wherein sequence B' is complementary to a nucleotide sequence B formed by extending the elongatable-primer hybridized to said portion of said polynucleotide using said polynucleotide as a template, wherein sequence B is immediately 5' of a sequence or nucleotide complementary to the mutation to be detected, wherein said sequence or nucleotide complementary to the mutation is formed by extending the elongatable-primer hybridized to said portion of said polynucleotide using said polynucleotide as a template,
wherein the counter-primer has a Tm less than sequence A and greater than the Tm of sequence B',
wherein the counter-primer hybridizes to the extended elongatable-primer at a site 3' of said sequence or nucleotide complementary to the mutation to be detected,
and wherein the Tm of sequence A is greater than the Tm of sequence B';
producing a target by subjecting the elongatable-primer and the counter-primer to an extension reaction using polymerase and using said polynucleotide as a template at a temperature less than the Tm of sequence A but greater than the Tm of sequence B';
denaturing the target to single-stranded form if the target produced in the step is not single-stranded, such that sequence B' hybridizes with sequence B in the extended elongatable-primer to form a stem-loop structure;

subjecting the stem-loop structure to a hybridization reaction with a probe which is fixed to an electrode, wherein the probe has a nucleic acid sequence at its 3' end that is complementary to the sequence or nucleotide complementary to the mutation to be detected;
subjecting the stem-loop structure and the probe to a ligation reaction to form a ligated target and probe;
performing a washing, a denaturing, or a washing and denaturing treatment after the ligation reaction;
forming a complementary strand hybridized to the ligated target and probe to form a double-stranded complex;
contacting the double-stranded complex with a double strand specific, electrochemically active intercalator;
and detecting the electrochemical response of the electrochemically active intercalator with the electrode thereby detecting the mutation.

2. The nucleotide mutation detection method according to claim 1, wherein the hybridization reaction is performed using a solution containing at least those salts required for hybridization of the nucleic acids.

3. The nucleotide mutation detection method according to claim 1, wherein the ligation reaction is performed using a synthetic enzyme solution containing at least salts sufficient to prevent dissociation of the double-strand nucleic acids formed by hybridization, DNA ligase, and the corresponding DNA ligase buffer solution.

4. The nucleotide mutation detection method according to claim 1, wherein the hybridization and ligation reactions are performed simultaneously using a synthetic enzyme solution containing at least DNA ligase and the corresponding DNA ligase buffer solution.

5. The nucleotide mutation detection method according to claim 1, wherein the denaturing operation of the washing, denaturing, or washing and denaturing treatment is performed using a denaturing agent or via thermal denaturing.

6. The method according to claim 1, wherein the nucleotide mutation is single nucleotide polymorphism.

7. The method according to claim 1, wherein the nucleotide mutation is short nucleotide tandem repeat mutation.

8. The method according to claim 1, wherein the nucleotide mutation is nucleotide deletion mutation.

9. The method according to claim 1, wherein the nucleotide mutation is nucleotide insertion mutation.

10. The method according to claim 1, wherein the nucleotide mutation is translocation mutation.

11. The method according to claim 1, wherein the probe is multiple types of probes comprising normal probe, single nucleotide deletion probe and single nucleotide mutation probe.

12. The method according to claim 1, wherein the target is amplified by performing Asymmetrical-Polymerase Chain Reaction (A-PCR).

* * * * *

SEQUENCE LISTING

<160> NUMBER OF SEQ ID NOS: 30

<210> SEQ ID NO 1
<211> LENGTH: 40
<212> TYPE: DNA
<213> ORGANISM: Homo sapiens

<400> SEQUENCE: 1
gaattagctg tatcgtcaag gcactcttgc ctacgccacc        40

<210> SEQ ID NO 2
<211> LENGTH: 40
<212> TYPE: DNA
<213> ORGANISM: Homo sapiens

<400> SEQUENCE: 2
gaattagctg tatcgtcaag gcactcttgc ctacgccacg        40

<210> SEQ ID NO 3
<211> LENGTH: 80
<212> TYPE: DNA
<213> ORGANISM: Homo sapiens

<400> SEQUENCE: 3
agctccaact accacggcct gctgaaaatg actgaatata aacttgtggt agttggagct        60
ggtggcgtag gcaagagtgc        80

<210> SEQ ID NO 4
<211> LENGTH: 80
<212> TYPE: DNA
<213> ORGANISM: Homo sapiens

<400> SEQUENCE: 4
agctccaact accacggcct gctgaaaatg actgaatata aacttgtggt agttggagct        60
cgtggcgtag gcaagagtgc        80

<210> SEQ ID NO 5
<211> LENGTH: 40
<212> TYPE: DNA
<213> ORGANISM: Homo sapiens

<400> SEQUENCE: 5
tgaattagct gtatcgtcaa ggcactcttg cctacgccac        40

<210> SEQ ID NO 6
<211> LENGTH: 46
<212> TYPE: DNA
<213> ORGANISM: Homo sapiens

<400> SEQUENCE: 6
agctccaact accacggcct gctgaaaatg actgaatata aacttg         46

<210> SEQ ID NO 7
<211> LENGTH: 24
<212> TYPE: DNA
<213> ORGANISM: Homo sapiens

<400> SEQUENCE: 7
ttctgaatta gctgtatcgt caag                                 24

<210> SEQ ID NO 8
<211> LENGTH: 46
<212> TYPE: DNA
<213> ORGANISM: Homo sapiens

<400> SEQUENCE: 8
agctccaact accacggcct gctgaaaatg actgaatata aacttg         46

<210> SEQ ID NO 9
<211> LENGTH: 40
<212> TYPE: DNA
<213> ORGANISM: Homo sapiens

<400> SEQUENCE: 9
gttgtcctag cacctgacgc ctcgttgtac atcagagacg                40

<210> SEQ ID NO 10
<211> LENGTH: 40
<212> TYPE: DNA
<213> ORGANISM: Homo sapiens

<400> SEQUENCE: 10
gttgtcctag cacctgacgc ctcgttgtac atcagagaca                40

<210> SEQ ID NO 11
<211> LENGTH: 108
<212> TYPE: DNA
<213> ORGANISM: Homo sapiens

<400> SEQUENCE: 11
gagcatttta caccttgaag accctccctt tggaatggca cagggtacgt cttcaaggtg    60
taaaatgctc cgtctctgat gtacaacgag gcgtcaggtg ctaggaca              108

<210> SEQ ID NO 12
<211> LENGTH: 86
<212> TYPE: DNA
<213> ORGANISM: Homo sapiens

<400> SEQUENCE: 12
cctccctttg gaatggcaca gggtacgtct tcaaggtgta aaatgctccg tctctgatgt    60
acaacgaggc gtcaggtgct aggaca                                        86

<210> SEQ ID NO 13
<211> LENGTH: 22
<212> TYPE: DNA
<213> ORGANISM: Homo sapiens

```
<400> SEQUENCE: 13
gagcatttta caccttgaag ac                                              22

<210> SEQ ID NO 14
<211> LENGTH: 40
<212> TYPE: DNA
<213> ORGANISM: Homo sapiens

<400> SEQUENCE: 14
gaattagctg tatcgtcaag gcactcttgc ctacgccacc                           40

<210> SEQ ID NO 15
<211> LENGTH: 40
<212> TYPE: DNA
<213> ORGANISM: Homo sapiens

<400> SEQUENCE: 15
gaattagctg tatcgtcaag gcactcttgc ctacgccacg                           40

<210> SEQ ID NO 16
<211> LENGTH: 81
<212> TYPE: DNA
<213> ORGANISM: Homo sapiens

<400> SEQUENCE: 16
agctccaact accacggcct gctgaaaatg actgaatata aacttgtggt agttggagct     60
cgtggcgtag gcaagagtgc c                                               81

<210> SEQ ID NO 17
<211> LENGTH: 79
<212> TYPE: DNA
<213> ORGANISM: Homo sapiens

<400> SEQUENCE: 17
agctccaact accacggcct gctgaaaatg actgaatata aacttgtggt agttggagct     60
cgtggcgtag gcaagagtg                                                  79

<210> SEQ ID NO 18
<211> LENGTH: 46
<212> TYPE: DNA
<213> ORGANISM: Homo sapiens

<400> SEQUENCE: 18
agctccaact accacggcct gctgaaaatg actgaatata aacttg                    46

<210> SEQ ID NO 19
<211> LENGTH: 20
<212> TYPE: DNA
<213> ORGANISM: Homo sapiens

<400> SEQUENCE: 19
ggcactcttg cctacgccac                                                 20

<210> SEQ ID NO 20
<211> LENGTH: 38
<212> TYPE: DNA
<213> ORGANISM: Homo sapiens

<400> SEQUENCE: 20
tggaggtact tttcagccag gatgtaacat tggagaag                             38
```

```
<210> SEQ ID NO 21
<211> LENGTH: 38
<212> TYPE: DNA
<213> ORGANISM: Homo sapiens

<400> SEQUENCE: 21
atggaggtac ttttcagcca ggatgtaaca ttggagaa                        38

<210> SEQ ID NO 22
<211> LENGTH: 87
<212> TYPE: DNA
<213> ORGANISM: Homo sapiens

<400> SEQUENCE: 22
ctatccgcgt gattgcctaa ataatattta cctccaagtc ctctctctgc aatcacgcgg   60
atagcttctc caatgttaca tcctggc                                      87

<210> SEQ ID NO 23
<211> LENGTH: 87
<212> TYPE: DNA
<213> ORGANISM: Homo sapiens

<400> SEQUENCE: 23
ctatccgcgt gattgcctaa ataatattta cctccaagtc ctctctctgc aatcacgcgg   60
atagcttctc caatgttaca tcctggc                                      87

<210> SEQ ID NO 24
<211> LENGTH: 48
<212> TYPE: DNA
<213> ORGANISM: Homo sapiens

<400> SEQUENCE: 24
ctatccgcgt gattgcctaa ataatattta cctccaagtc ctctctct               48

<210> SEQ ID NO 25
<211> LENGTH: 38
<212> TYPE: DNA
<213> ORGANISM: Homo sapiens

<400> SEQUENCE: 25
catcgtccac tcagccactg gatttaagca gagttcaa                          38

<210> SEQ ID NO 26
<211> LENGTH: 38
<212> TYPE: DNA
<213> ORGANISM: Homo sapiens

<400> SEQUENCE: 26 gaagggctg tcctcgtcct ccagctgtta tctggaag                           38

<210> SEQ ID NO 27
<211> LENGTH: 80
<212> TYPE: DNA
<213> ORGANISM: Homo sapiens

<400> SEQUENCE: 27
aagcccttca gcggccctga ggctcaaagt cagatgctac tggcctctga agggcttttg   60
aactctgctt aaatccagtg                                              80

<210> SEQ ID NO 28
<211> LENGTH: 117
<212> TYPE: DNA
```

-continued

```
<213> ORGANISM: Homo sapiens

<400> SEQUENCE: 28
aagcccttca gcggccctga ggctcaaagt cagatgctac tggcctctga agggcttttg        60
aactctgctt aaatccagtg gctgagtgga cgatgacatt cagaaaccca tagagcc         117

<210> SEQ ID NO 29
<211> LENGTH: 42
<212> TYPE: DNA
<213> ORGANISM: Homo sapiens

<400> SEQUENCE: 29
aagcccttca gcggccctga ggctcaaagt cagatgctac tg                          42

<210> SEQ ID NO 30
<211> LENGTH: 22
<212> TYPE: DNA
<213> ORGANISM: Homo sapiens

<400> SEQUENCE: 30
cactggattt aagcagagtt ca                                                22
```